US007700332B1

(12) United States Patent
Rajgarhia et al.

(10) Patent No.: US 7,700,332 B1
(45) Date of Patent: *Apr. 20, 2010

(54) METHODS FOR THE SYNTHESIS OF LACTIC ACID USING CRABTREE-NEGATIVE YEAST TRANSFORMED WITH THE LACTATE DEHYDROGENASE GENE

(75) Inventors: Vineet Rajgarhia, Minnetonka, MN (US); Vassily Hatzimanikatis, Minneapolis, MN (US); Stacey Olson, Minneapolis, MN (US); Ting Carlson, Dayton, OH (US); John N. Starr, Chaska, MN (US); Jeffrey J. Kolstad, Wayzata, MN (US); Aharon Eyal, Jerusalem (IL)

(73) Assignee: Cargill Inc., Wayzata, MN (US)

( * ) Notice: Subject to any disclaimer, the term of this patent is extended or adjusted under 35 U.S.C. 154(b) by 90 days.

This patent is subject to a terminal disclaimer.

(21) Appl. No.: 11/788,839

(22) Filed: Apr. 20, 2007

Related U.S. Application Data

(63) Continuation of application No. 10/287,564, filed on Nov. 4, 2002, now Pat. No. 7,229,805, which is a continuation of application No. 09/574,873, filed on May 19, 2000, now Pat. No. 6,485,947, which is a continuation-in-part of application No. 09/316,490, filed on May 21, 1999, now abandoned.

(51) Int. Cl.
*C12P 7/60* (2006.01)
*C12N 1/16* (2006.01)

(52) U.S. Cl. ........................................ 435/139; 435/41
(58) Field of Classification Search ........................ None
See application file for complete search history.

(56) References Cited

U.S. PATENT DOCUMENTS

| 4,275,234 | A | 6/1981 | Baniel et al. |
|---|---|---|---|
| 4,806,472 | A | 2/1989 | de Louvencourt et al. |
| 4,859,596 | A | 8/1989 | Hollenberg et al. |
| 4,943,529 | A | 7/1990 | Van den Berg et al. |
| 5,510,526 | A | 4/1996 | Baniel et al. |
| 5,641,406 | A | 6/1997 | Sarhaddar et al. |
| 5,712,152 | A | 1/1998 | Dequin et al. |
| 5,783,423 | A | 7/1998 | Wood et al. |
| 5,789,184 | A | 8/1998 | Fowlkes et al. |
| 5,817,502 | A | 10/1998 | Ligon et al. |
| 5,831,122 | A | 11/1998 | Eyal |
| 5,843,760 | A | 12/1998 | Zhang et al. |
| 5,866,371 | A | 2/1999 | Badziong et al. |
| 5,866,382 | A | 2/1999 | Hallborn et al. |
| 5,876,951 | A | 3/1999 | Fowlkes et al. |
| 5,882,884 | A | 3/1999 | Cho |
| 6,485,947 | B1 * | 11/2002 | Rajgarhia et al. ............ 435/139 |
| 7,109,010 | B2 * | 9/2006 | Rajgarhia et al. ............ 435/190 |
| 7,229,805 | B2 * | 6/2007 | Rajgarhia et al. ............ 435/139 |

FOREIGN PATENT DOCUMENTS

| EP | 0 370 160 A2 | 5/1990 |
|---|---|---|
| WO | WO 93/00440 | 1/1993 |
| WO | WO 94/00554 | 1/1994 |
| WO | WO 94/01569 | 1/1994 |
| WO | WO 97/16528 | 5/1997 |
| WO | WO 98/26079 | 6/1998 |
| WO | WO 98/54337 | 12/1998 |
| WO | WO 99/14335 | 3/1999 |
| WO | WO 00/14258 | 3/2000 |

OTHER PUBLICATIONS

"36.12. *Kluyveromyces thermotolerans* (Filippov) Yarrow (1972)", The Yeasts, A Taxonomic Study, Elsevier, Fourth Edition, pp. 240-241 (1998).
"Yeast Metabolism", Yeast Physiology and Biotechnology, Chapter 5, pp. 203-264 (Date Unknown).
Adachi, E. et al., "Modification of Metabolic Pathways of *Saccharomyces cerevisiae* by the Expression of Lactate Dehydrogenase and Deletion of Pyruvate Decarboxylase Genes for the Lactic Acid Fermentation at Low pH Value", Journal of Fermentation and Bioengineering, vol. 86, No. 3, pp. 284-289 (1998).
Becker, D. et al., "High-Efficiency Transformation of Yeast by Electroporation", Methods in Enzymology, vol. 194, pp. 182-187 (1991).
Bianchi, M. et al., "The 'petite-negative' yeast *Kluyveromyces lactis* has a single gene expressing pyruvate decarboxylase activity", Molecular Microbiology, vol. 19, No. 1, pp. 27-36 (1996).
Billard, P. et al., "Isolation and characterization of the gene encoding xylose reductase from *Kluyveromyces lactis*", Gene, vol. 162, No. 1, pp. 93-97 (1995).
Brambilla, L. et al., "High Production of Lactic Acid from Metabolically Engineered *Saccharomyces cerevisiae*", Advances in Bioprocess Engineering, pp. 417-423 (1994).
Cho. J. et al., "*Pichia stipitis* Genes for Alcohol Dehydrogenase with Fermentative and Respiratory Functions", Applied and Environmental Microbiology, vol. 64, No. 4, pp. 1350-1358 (Apr. 1998).
Danner, H. et al., "Biotechnological Production of Acrylic Acid from Biomass" Applied Biochemistry and Biotechnology, vol. 70-72, pp. 887-894 (1998).
Dequin, S. et al., "Mixed Lactic Acid-Alconholic Fermentation by *Saccharomyes cerevisiae* Expressing the *Lactobacillus casei* L(+)-LDH", Bio/Technology, vol. 12, pp. 173-177 (Feb. 1994).
Destruelle, M. et al., "Regulation of the Expression of the *Kluyveromyces lactis* PDC1 Gene: Carbon Soure Responsive Elements and Autoregulation", Yeast, vol. 15, No. 5, pp. 361-370 (Mar. 30, 1999).
Durrens, P. et al., "Expression of the avian gag-myc oncogene in *Saccharomyces cerevisiae*", Current Genetics, vol. 18, No. 1 pp. 7-12 (Jul. 1990).

(Continued)

*Primary Examiner*—Anand U Desai
(74) *Attorney, Agent, or Firm*—Gary C. Cohn PLLC

(57) ABSTRACT

The invention provides methods and materials related to the production of lactic acid. Specifically, the invention provides methods for producing lactic acid using a crabtree-negative yeast, such as of the *Kluyveromyces, Pichia, Candida, Trichosporon* and *Yamadazmya* genera, which have been transformed with a lactate dehydrogenase gene.

4 Claims, 17 Drawing Sheets

OTHER PUBLICATIONS

Flikweert, M. et al., "Pyruvate Decarboxylase: An Indispensable Enzyme for Growth of *Saccharomyces cerevisiae* on Glucose", Yeast, vol. 12, pp. 247-257 (1996).

Flikweert, M. et al., "Metabolic Responses of Pyruvate Decarboxylase-Negative *Saccharomyces cerevisiae* to Glucose Excess", Applied and Environmental Microbiology, vol. 63, No. 9, pp. 3399-3404 (Sep. 1997).

Garmyn, D. et al., "Cloning, Nucleotide Sequence, and Transcriptional Analysis of the *Pediococcus acidilactici* L-(+)-Lactate Dehydrogenase Gene", Applied and Environmental Microbiology, vol. 61, No. 1, pp. 266-272 (Jan. 1995).

Gonzalez, F. et al., "Molecular cloning of TvDAO1, a Gene Encoding a D-Amino Acid Oxidase from *Trigonopsis variabilis* and its Expression in *Saccharomyces cerevisiae* and *Kluyveromyces lactis*", Yeast, vol. 13, pp. 1399-1408 (1997).

Gunge, N. et al., "Isolation and Characterization of Linear Deoxyribonucleic Acid Plasmids from *Kluyveromyces lactis* and the Plasmid-Associated Killer Character", Journal of Bacteriology, vol. 145, No. 1, pp. 382-390 (Jan. 1981).

Gunge, N. et al., "Replication and Maintenance of the *Kluyveromyces linear* pGKL Plasmids", European Journal of Epidemiology, vol. 4, No. 4, pp. 409-414 (Sep. 1988).

Hohmann, S., "Characterization of PDC6, a Third Structural Gene for Pyruvate Decarboxylase in *Saccharomyces cerevisiae*", Journal of Bacteriology, vol. 173, No. 24, pp. 7963-7969 (Dec. 1991).

Hohmann, S., "Characterisation of PDC2, a gene necessary for high level expression of pyruvate decarboxylase structural genes in *Saccharomyces cerevisiae*", Mol. Gen. Genet., vol. 241, pp. 657-666 (1993).

Hsieh, H. et al., "An autoselection system in recombinant *Kluyveromyces lactis* enhances cloned gene stability and provides freedom in medium selection", Appl. Microbiol. Biotechnol., vol. 49 No. 2, pp. 147-152 (1998).

Hsieh, H. et al., "Partial-pKD1 plasmids provide enhanced structural stability for heterologous protein production in *Kluyveromyces lactis*", Appl. Microbiol. Biotechnol., vol. 49, No. 4, 411-416 (1998).

Ito, H. et al., "Transformation of Intact Yeast Cells Treated with Alkali Cations", Journal of Bacteriology, vol. 153, No. 1, pp. 163-168 (Jan. 1983).

Kiers, J. et al., "Regulation of Alcoholic Fermentation in Batch and Chemostat Cultures of *Kluyveromyces lactis* CBS 2359", Yeast, vol. 14, No. 5, pp. 459-469 (Mar. 30, 1998).

Lightelm, M. et. al., "The effect of respiratory inhibitors on the fermentative ability of *Pichia stipitis, Pachysolen tannophilus* and *Saccharomyces cerevisiae* under various conditions of aerobiosis", Appl. Microbiol. biotechnol., vol. 29, pp. 67-71 (1988).

Morsomme, P. et al., "Single point mutations in various domains of a plant plasma membrane H+-ATPase expressed in *Saccharomyces cerevisiae* increase H+-pumping and permit yeast growth at low pH", The EMBO Journal, vol. 15, No. 20, pp. 5513-5526 (Oct. 15, 1996).

Seeboth, P. et al., "pdc1⁰ Mutants of *Saccharomyces cerevisiae* Give Evidence for an Additional Structural PDC Gene: Cloning of PDC5, a Gene Homologous to PDC1", Journal of Bacteriology, vol. 172 No. 2 pp. 678-685 (Feb. 1990).

Shi, N. et al., "Anaerobic growth and improved fermentation of *Pichia stipitis* bearing a URA1 gene from *Saccharomyces cerevisiae*", Appl. Microbiol. Biotechnol., vol. 50, pp. 339-345 (1998).

Siso, M. et al., "Reoxidation of the NADPH produced by the pentose phosphate pathway is necessary for the utilization of glucose by *Kluveromyces lactis* rag2 mutants", FEBS Letters, vol. 387, pp. 7-10 (1996).

Subden, R. et al., "An L-lactice acid dehydrogenase based method for detecting microbial colonies performing a malo-lactic fermentation", Canadian Journal of Microbiology, vol. 28, No. 7, pp. 883-886 (Jul. 1982).

Ullrich, J., "Yeast Pyruvate Decarboxylase (2-Oxoacid Carboxylyase, EC 4.1.1.1) Assay of Thiamine Pyrophosphate", Methods in Enzymology vol. XVIII Vitamins and Coenzymes Part A, Academic Press, pp. 109-115 (1970).

Van Hoek, P. et al., "Effects of Pyruvate Decarboxylase Overproduction on Flux Distribution at the Pyruvate Branch Point in *Saccharomyces cerevisiae*", Applied and Environmental Microbiology, vol. 64, No. 6, pp. 2133-2140 (Jun. 1998).

Warnecke, D. et al., "Cloning and Functional Expression of UGT Genes Encoding Sterol Glucosly transferases from *Saccharomyces cerevisiae, Candida albicans, Pichia pastoris*, and *Dictyostelium discoideum*", The Journal of Biological Chemistry, vol. 274, No. 19 pp. 13048-13059 (May 7, 1999).

Wesolowski-Louvel, M. et al., "*Kluyveromyces lactis*", Nonconventional Yeasts in Biotechnology, A Handbook, Chapter 5, Klaus Wolf ed., Springer-Veriag, pp. 139-201 (1996).

Witte, V. et al., "Characterization of yeasts with high L[+]-lactic acid production : Lactic acid specific soft-agar overlay (LASSO) and TAFE-patterns"< J. Basic Microbiol, vol. 29, No. 10, pp. 707-716(1989).

Zeeman, A. et al., "Inactivation of the *Kluyveromyces lactis* KIPDAI gene leads to loss of pyruvate dehydrogenase activity, impairs growth on glucose and triggers aerobic alcoholic fermentation", Microbiology, vol. 144, pp. 3437-3446 (1998).

Porro, D. et al., "Development of Metabolically Engineered *Saccharomyces cerevisiae* Cells for the Production of Lactic Acid", Biotechnol. Prog., vol. 11, No. 3, pp. 294-298 (May 1, 1995).

Stewart, J., "A Chemist's Perspective on the Use of Genetically Engineered Microbes As Reagents for Organic Synthesis", Biotechnology and Genetic Engineering Reviews, vol. 14, pp. 67-143 (Apr. 1, 1997).

Urk, H. et al., "Transient-State Analysis of Metabolic Fluxes in Crabtree Positive and Crabtree-Negative Yeasts", Applied and Environmental Microbiology, vol. 56, No. 1, pp. 281-287 (1990).

Franzblau et al. Induction of fermentation in Crabtree-negative yeasts. Mycopathologia (1983) 82:185-190.

Passoth et al. Peculiarities of the Regulation of Fermentation and Respiration in the Crabtree-Negative, Xylose-Fermenting Yeast *Pichia stipitis*. Applied Biochemistry and Biotechnology (1996) 57/58:201-211.

Lighthelm et al. The effect of respiratory inhibitors on the fermentative ability of *Pichia stipitis, Pachysolen tannophilus* and *Saccharomyces cerevisiae* under various conditions of aerobiosis. Appl. Microbiol. Biotechnol. (1988) 29:67-71.

Siso et al. Reoxidation of the NADPH produced by the pentose phosphate pathway is necessary for the utiliation of glucose by *Kluyveromyces lactis* rag2mutants FEBS Letters (1996) 387:7-10.

Gonzalex et al. molecular Cloning of TvDAO1, a gene Encoding a D-Amino Acid Oxidase from *Trigonopsis variabilis* and its Expresion in *Saccharomyces cerevisiae* and *Kluyveromyces lactis*. Yeast (1997) 13: 1399-1408.

Shi et al. Anaerobic growth and improved fermentation of *Pichia stipitis* bearing a URA 1 gene from *Saccharomyces cerevisiae*. Appl. Microbiol Blotechnol. (1998) 50: 339-345.

\* cited by examiner

A

B

C

METHODS FOR THE SYNTHESIS OF LACTIC ACID USING CRABTREE-NEGATIVE YEAST TRANSFORMED WITH THE LACTATE DEHYDROGENASE GENE

This application is a continuation of U.S. patent application Ser. No. 10/287,564, entitled METHODS FOR THE SYNTHESIS OF LACTIC ACID USING CRABTREE-NEGATIVE YEAST TRANSFORMED WITH THE LACTATE DEHYDROGENASE GENE filed 4 Nov. 2002, now U.S. Pat. No. 7,229,805, which is a continuation of U.S. patent application Ser. No. 09/574,873, entitled 'PRODUCTION OF LACTATE USING CRABTREE NEGATIVE ORGANISMS IN VARYING CULTURE CONDITIONS", filed May 19, 2000, now U.S. Pat. No. 6,485,947, which is a continuation-in-part of U.S. patent application Ser. No. 09/316,490, entitled "METHODS AND MATERIALS FOR THE SYNTHESIS OF ORGANIC PRODUCTS", filed May 21, 1999, now abandoned the disclosure of which is hereby incorporated in its entirety herein.

BACKGROUND

1. Technical Field

The invention relates to methods and materials involved in the production of organic products.

2. Background Information

Organic products such as lactic acid have many important industrial uses. For example, organic acids can be used to synthesize plastic materials as well as other products. To meet the increasing need for organic products, more efficient and cost effective production methods are being developed. One such method involves the use of bacteria. Specifically, certain bacteria can produce large quantities of particular organic products under certain fermentation conditions. The use of living bacteria as factories, however, is limited by the inability of the bacteria to grow as the organic product accumulates in the growth media. To circumvent such limitations, various product purification techniques have been employed during product synthesis. In addition, the use of microorganisms other than bacteria has been attempted. In fact, *Saccharomyces cerevisiae*, which is known to be acid tolerant, has been genetically modified in an attempt to produce lactic acid. Specifically, *S. cerevisiae* cells were modified by providing the cells with a bovine lactate dehydrogenase cDNA and disrupting endogenous pyruvate decarboxylase genes (PDC1, PDC5, and PDC6). While these modified *S. cerevisiae* cells produced some lactic acid, cell growth was suppressed leading to the conclusion that both cell growth and lactic acid production need improvement.

SUMMARY

The present invention relates generally to methods and materials for producing organic products. Specifically, the invention provides yeast cells, methods for culturing yeast cells, methods for making yeast cells, nucleic acid constructs, and methods and materials for producing various organic products. The invention is based on the discovery that particular microorganisms (e.g., bacterial and fungal microorganisms) can be genetically manipulated such that they have the ability, under specific culture conditions, to grow, utilize various carbon sources for growth as well as product production, and produce a desired organic product for commercial purposes. For example, the yeast cells provided herein can grow and produce an organic product when cultured at low pH and high temperature. Having the ability to grow rapidly and produce an organic product efficiently under, for example, low pH and high temperature conditions is particularly advantageous. Specifically, the ability of a microorganism to tolerate low pH obviates the need to maintain a neutral pH environment, which can be difficult and expensive during large-scale production processes. In addition, the methods and materials needed to recover the desired organic product from a low pH broth can be more practical and efficient than those required to recover the same organic product from a broth having a more neutral pH. For example, certain organic acid products can precipitate out of solution as the pH drops below the product's pKa value, making recovery quite simple. Further, the ability of a microorganism to tolerate high temperatures obviates the need to maintain cool temperatures during the growth and production phases. Clearly, reducing the need to lower the temperature in a large volume tank of broth during large-scale production processes makes the overall process more efficient and less expensive. Moreover, the ability of a microorganism to tolerate both low pH and high temperature provides a convenient method for preventing contamination by other less tolerant microorganisms during the large-scale production processes.

It is important to note that a critical aspect relating to the ability to produce a desired organic product for commercial purposes can be the specific productivity at which that desired organic product is produced. For example, providing a high specific productivity using the methods and materials as described herein can allow a microorganism to generate the energy needed for cell maintenance when exposed to culture conditions such as low pH and high temperature. This required energy can be generated via a fermentation pathway under substantially anaerobic conditions, rather than relying on the generation of energy via the respiratory pathway. Obtaining energy via a fermentation pathway is particularly advantageous when producing an organic product that does not require the respiratory pathway since essentially all of the provided carbon source can be used to produce the desired organic product.

The invention also is based on the discovery that the utilization of a carbon source by certain genetically manipulated microorganisms can be controlled and directed predominately towards the production of either biomass or a desired organic product. In general terms, the invention involves two types of culturing processes. One culturing process involves culturing microorganisms under specific culture conditions, depending on the microorganism and desired outcome, that promote biomass production, while the other involves a different set of culture conditions, also dependent upon the microorganism and desired outcome, that promotes the production of a desired organic product. Clearly, having the ability to manipulate the utilization of a carbon source during large-scale production processes provides manufacturers with greater flexibility and more control than is otherwise possible.

In addition, the invention is based on the discovery that certain microorganisms can be genetically manipulated such that most, if not all, of a carbon source is utilized for the production of either biomass or a desired organic product. Specifically, the invention provides yeast cells that are modified such that biosynthesis pathways that divert the utilization of a carbon source away from the production of biomass or the desired organic product are inactivated. Inactivating such biosynthesis pathways provides microorganisms that can efficiently grow and produce the desired product.

In general, the invention features a yeast cell containing an exogenous nucleic acid molecule, with the exogenous nucleic acid molecule encoding a polypeptide having enzymatic activity within the cell. The nucleic acid can be incorporated into the genome of the cell. The enzymatic activity leads to the formation of an organic product that, in some embodiments, is secreted from the cell. The cell further has a crabtree-negative phenotype and produces the organic product. The cell can be, for example, from the genus *Kluyveromyces, Pichia, Hansenula, Candida, Trichosporon,* or *Yamadazyma*. The organic product can be, for example, a fermentation product, a pyruvate-derived product, an organic acid, or a carboxylate such as lactate. In one embodiment, the polypeptide can have lactate dehydrogenase activity. For example, the exogenous nucleic acid can encode a bacterial lactate dehydrogenase or fungal lactate dehydrogenase such as a *K. lactis* fungal lactate dehydrogenase.

In another embodiment, the cell contains four exogenous nucleic acid molecules, each of the four exogenous nucleic acid molecules encoding a different polypeptide. For example, the first of the four exogenous nucleic acid molecules can encode a first polypeptide having lactate dehydrogenase activity, the second can encode a second polypeptide having CoA-transferase activity, the third can encode a third polypeptide having lactyl-CoA dehydratase activity, and the fourth can encode a fourth polypeptide having acrylyl-CoA hydratase activity. Such a cell can produce acrylate as the carboxylate product. Alternatively, the first of the four exogenous nucleic acid molecules can encode a first polypeptide having 2-dehydro-3-deoxy-D-pentanoate aldolase activity, the second can encode a second polypeptide having xylonate dehydratase activity, the third can encode a third polypeptide having xylonolactonase activity, and the fourth can encode a fourth polypeptide having D-xylose dehydrogenase activity. Such a cell can produce a carbohydrate, such as D-xylose, as the organic product.

In yet another embodiment, the cell contains six exogenous nucleic acid molecules, each of the six exogenous nucleic acid molecules encoding a different polypeptide. For example, the first of the six exogenous nucleic acid molecules can encode a first polypeptide having 2,5-dioxovalerate dehydrogenase activity, the second can encode a second polypeptide having 5-dehydro-4-deoxy-D-glucarate dehydrogenase activity, the third can encode a third polypeptide having glucarate dehydratase activity, the fourth can encode a fourth polypeptide having aldehyde dehydrogenase activity, the fifth can encode a fifth polypeptide having glucuronolactone reductase activity, and the sixth can encode a sixth polypeptide having L-gulonolactone oxidase activity. Such a cell can produce a vitamin, for example L-ascorbate, as the organic product.

The organic product can contain more than three carbon atoms, and can be, for example, an amino acid.

In another embodiment, the cell is able to catabolize a pentose carbon such as ribose, arabinose, xylose, and lyxose.

In another embodiment the cell has reduced pyruvate decarboxylase activity or reduced alcohol dehydrogenase activity. For example, the cell can lack all pyruvate decarboxylase activity. The reduced pyruvate decarboxylase activity can be due to a disrupted genetic locus, where the locus normally has the nucleic acid sequence that encodes pyruvate decarboxylase. Alternatively, the cell could contain an antisense molecule, such as a ribozyme, that corresponds to an endogenous nucleic acid sequence, where the antisense molecule reduces the pyruvate decarboxylase activity. The cell can also contain an additional exogenous nucleic acid molecule that functions as a killer plasmid.

In another embodiment, the enzymatic activity of the polypeptide encoded by the exogenous nucleic acid leads to the formation of the organic product in an NADH-consuming manner.

In another embodiment, the cell produces at least about 60 grams of the organic product for every 100 grams of glucose consumed when the cell is cultured under optimal conditions for the production of the organic product.

In another aspect, the invention features a cell, e.g., a yeast cell, which contains an exogenous nucleic acid molecule, where the exogenous nucleic acid molecule encodes a polypeptide that promotes catabolism of a pentose carbon by the cell. The polypeptide can be, for example, xylose reductase, xylitol dehydrogenase, or xylulokinase, and the pentose carbon can be, for example, ribose, arabinose, xylose, and lyxose. The cell can further catabolize a hexose carbon and can, if desired, simultaneously catabolize the hexose carbon and the pentose carbon. The hexose carbon can be, for example, allose, altrose, glucose, mannose, gulose, iodose, fructose, galactose, and talose.

In another aspect, the invention features a yeast cell containing an exogenous nucleic acid molecule, where the exogenous nucleic acid molecule encodes a polypeptide that promotes accumulation of acetyl-CoA in the cytoplasm of the cell. The polypeptide can be a polypeptide that has citrate lyase activity, or can be a mitochondrial membrane polypeptide that promotes acetyl-CoA permeability across the mitochondrial membrane. The cell can have reduced pyruvate decarboxylase activity or reduced alcohol dehydrogenase activity. Alternatively, the yeast cell can lack ethanol production, and can have a growth rate under culture conditions lacking ethanol and acetate that is greater than the growth rate observed for a comparable yeast cell lacking ethanol production.

In yet another aspect, the invention features a yeast cell having reduced activity of a mitochondrial polypeptide, where the cell has a crabtree-negative phenotype. Such a cell can be from, for example, the genus *Kluyveromyces, Pichia, Hansenulo, Candida, Trichosporon,* or *Yamadazyma*. The cell can completely lack the activity. The cell can contain a disrupted locus, where the locus normally includes a nucleic acid sequence that encodes the mitochondrial polypeptide. The mitochondrial polypeptide can be a Krebs cycle enzyme. Further, the cell can accumulate a Krebs cycle product. The cell can include an exogenous nucleic acid molecule, where the exogenous nucleic acid molecule encodes a polypeptide having enzymatic activity within the cell, with the enzymatic activity leading to formation of an organic product, such that the cell produces the organic product. The organic product can be, for example, citrate, α-ketoglutarate, succinate, fumarate, malate, and oxaloacetate. The polypeptide can be a polypeptide that participates in the catabolism of lactate or acetate.

In another aspect, the invention features a method for producing an organic product. The method includes providing yeast cells, where the cells include an exogenous nucleic acid molecule that encodes a polypeptide having enzymatic activity within the cells, where the enzymatic activity leads to the formation of the organic product, and where the cells have a crabtree-negative phenotype, and culturing the cells with culture medium such that the organic product is produced. The yeast cells can be from within the genus *Kluyveromyces, Pichia, Hansenula, Candida, Trichosporon,* or *Yamadazyma*. The organic product can be a fermentation product, a pyruvate-derived product, an organic product containing more than three carbon atoms, a carboxylate, carbohydrate, amino acid, vitamin, or lipid product. The organic product further can be lactate, glycerol, acrylate, xylose, ascorbate, citrate, isocitrate, α-ketoglutarate, succinyl-CoA, succinate, fumarate, malate, or oxaloacetate. In some embodiments, the organic product is secreted by the cells. The method can result in cells having reduced pyruvate decarboxylase activity or reduced alcohol dehydrogenase activity. The enzymatic activity can lead to the formation of the organic product in an NADH-consuming manner.

Cells made by these methods can produce at least about 60 grams of the organic product for every 100 grams of glucose consumed when the culturing step is optimal for production of the organic product. The culture medium, which can be liquid, can include an inhibitor of cellular respiration, such as antimycin A, cyanide, or azide. The culturing step can include growing the cells under aerobic growth conditions followed by contacting said cells with an inhibitor of cellular respiration.

In an alternative embodiment, the culturing step includes incubating the cells under anaerobic culture conditions. In a further alternative embodiment, the culturing step includes growing the cells under aerobic growth conditions followed by incubating the cells under anaerobic culture conditions. The culturing step can also include culturing the cells at a temperature greater than about 35° C.

In one embodiment, the culture medium has an organic pH value less than about 3.0, and/or an inorganic pH value less than about 3.0. In another embodiment, the medium contains a pentose carbon such as ribose, arabinose, xylose, or lyxose. The medium also can include a corn fiber hydrolysate having, for example, a pH value between about 2.0 and about 6.5.

In another aspect, the invention features a method for producing an organic product, the method including a) providing yeast cells containing an exogenous nucleic acid molecule encoding a polypeptide that promotes catabolism of a pentose carbon by the cell, where the cell contains an enzymatic activity that leads to the formation of said organic product, and b) culturing the cells with culture medium such that the organic product is produced.

In yet another aspect, the invention features a method for producing an organic product, the method including a) providing yeast cells, where the cells include an exogenous nucleic acid molecule encoding a polypeptide that promotes accumulation of acetyl-CoA in the cytoplasm of the cell, and where the cell contains an enzymatic activity that leads to the formation of the organic product, and b) culturing the cells with culture medium such that the organic product is produced.

In another aspect, the invention features a method for producing an organic product, the method including a) providing yeast cells having reduced activity of a mitochondrial enzyme, wherein reduction of the activity leads to the accumulation of the organic product, and b) culturing said cells with culture medium such that said organic product is produced.

In another aspect, the invention features a method for culturing yeast cells having a crabtree-negative phenotype, the method including culturing the cells with culture medium, where the culture medium has an organic pH value less than about 3.0 and/or an inorganic pH value less than about 3.0. The culturing step can include culturing the cells at a temperature greater than about 35° C. The culture medium can include an inhibitor of cellular respiration. The culture medium also can include a pentose carbon. In another embodiment, the culture medium can include a corn fiber hydrolysate.

In another aspect, the invention features a method for culturing yeast cells having a crabtree-negative phenotype, the method including culturing the cells with culture medium, where the culture medium includes a corn fiber hydrolysate.

In another aspect, the invention features a method for culturing yeast cells having a crabtree-negative phenotype, the method including culturing the cells with culture medium at a temperature greater than about 35° C., with the culture medium having an inorganic pH value less than about 3.0.

In another aspect, the invention features a method for culturing yeast cells having a crabtree-negative phenotype, the method including culturing the cells with culture medium at a temperature greater than about 35° C., with the culture medium including a pentose carbon.

In another aspect, the invention features a method for culturing yeast cells having a crabtree-negative phenotype, the method including culturing the cells with culture medium at a temperature greater than about 35° C., with the culture medium including a corn fiber hydrolysate.

In another aspect, the invention features a nucleic acid construct that includes a recombination sequence and a selected sequence, with the recombination sequence corresponding to a genomic sequence of a cell having a crabtree-negative phenotype, with the genomic sequence encoding an enzyme expressed by the cell, and with the selected sequence encoding an enzyme that leads to the formation of an organic product within the cell. The selected sequence can be within the recombination sequence such that the selected sequence is flanked on each end by the recombination sequence.

In another aspect, the invention features a method for making a recombinant yeast cell, including providing a yeast cell having a crabtree-negative phenotype, selecting an end product, identifying which exogenous enzyme or enzymes need to be added to the cell to produce the end product, identifying which endogenous enzyme or enzymes whose activity is to be reduced in said cell to allow production of said end product within said cell, adding the identified exogenous enzyme or enzymes to the provided yeast cell, and reducing the activity of the identified endogenous enzyme or enzymes in the provided yeast cell such that the cell produces the end product under culture conditions.

In another aspect, the invention features a corn fiber hydrolysate, the hydrolysate having a pH value between about 2.0 and about 6.5. The hydrolysate can include glucose, xylose, and arabinose. The hydrolysate can include about 40 grams/L glucose, about 40 grams/L xylose, and about 20 grams/L arabinose. Alternatively, the hydrolysate can include about 38.7 grams/L glucose, about 39.1 grams/L xylose, about 20.7 grams/L arabinose, and about 1.6 grams/L furfural.

In another aspect, the invention features a method for making an organic product, including a) culturing a microorganism under culture conditions, where the microorganism has reduced enzymatic activity; the enzymatic activity can be pyruvate decarboxylase, alcohol dehydrogenase, aldehyde dehydrogenase, or acetyl-CoA synthase activity; the microorganism exhibits a growth rate in the absence of ethanol and acetate that is at least about 30 percent of that observed for a corresponding microorganism not having said reduced enzymatic activity, and b) changing the culture conditions to promote production of the organic product.

In another aspect, the invention features a method for making an organic product, including a) culturing a microorganism under culture conditions that promote cellular respiration, where the microorganism has reduced enzymatic activity; the enzyme activity can be pyruvate decarboxylase, alcohol dehydrogenase, aldehyde dehydrogenase, or acetyl-CoA synthase activity, with the microorganism exhibiting a growth rate in the absence of ethanol and acetate that is at least about 30 percent of that observed for a corresponding microorganism not having such reduced enzymatic activity, and b) changing the culture conditions to reduce cellular respiration, thereby promoting production of the organic product.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
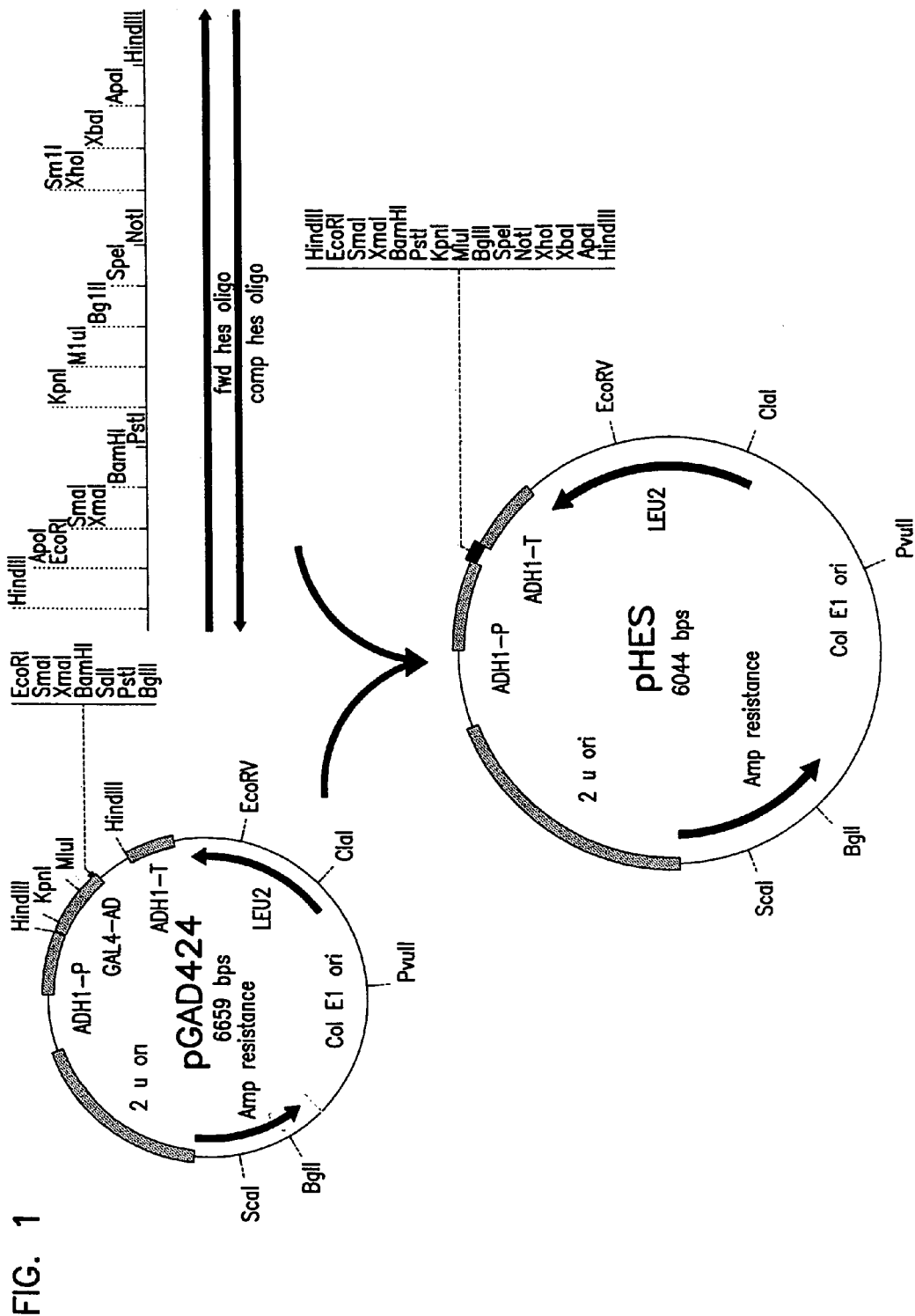
FIG. 1 is a diagram depicting the pHES plasmid.

The invention provides methods and materials related to the production of organic products. Specifically, the invention provides yeast cells, methods for culturing yeast cells, methods for making yeast cells, nucleic acid constructs, and methods and materials for producing various organic products.

The yeast cells provided herein can be used to produce organic products. Such organic products can be used in a wide range of applications. For example, organic products produced by the yeast cells described herein can be used as preservatives or additives in food, pharmaceutical, or cosmetic products, and can be used to make plastic as well as other products.

For the purpose of this invention, an organic product is any compound containing a carbon atom. For example, carboxylates (e.g., lactate, acrylate, citrate, isocitrate, alpha-ketoglutarate, succinate, fumarate, malate, oxaloacetate), carbohydrates (e.g., D-xylose), alditols (e.g., xylitol, arabitol, ribitol), amino acids (e.g., glycine, tryptophan, glutamate), lipids, esters, vitamins (e.g., L-ascorbate), polyols (e.g., glycerol, 1,3-propanediol, erythritol), aldehydes, alkenes, alkynes, and lactones are organic products. Thus, an organic product can contain one, two, three, four, five, six, seven, eight, nine, ten or more carbon atoms. In addition, organic products can have a molecular weight that is less than about 1,000 (e.g., less than about 900, 800, 700, 600, 500, 400, 300, 200, or 100). For example, D-xylose ($C_5H_{10}O_5$) is an organic product that has a molecular weight of 150. Further, organic products can be fermentation products. The term "fermentation product" as used herein refers to any organic compound that is produced by a fermentation process.

In general terms, a fermentation process involves the anaerobic enzymatic conversion of organic compounds such as carbohydrates to compounds such as ethyl alcohol, resulting in energy in the form of adenosine triphosphate (ATP). Thus, fermentation differs from cellular respiration in that organic products rather than molecular oxygen are used as electron acceptors. Examples of fermentation products include, without limitation, acetate, ethanol, butyrate, and lactate.

Organic products also can be pyruvate-derived products. The term "pyruvate-derived product" as used herein refers to any compound that is synthesized from pyruvate within no more than fifteen enzymatic steps. An enzymatic step is any chemical reaction or series of reactions catalyzed by a polypeptide having enzymatic activity. The term "polypeptide having enzymatic activity" as used herein refers to any polypeptide that catalyzes a chemical reaction of other substances without itself being destroyed or altered upon completion of the reaction or reactions. Typically, an enzymatic polypeptide catalyzes the formation of one or more products from one or more substrates. Such polypeptides can have any type of enzymatic activity including, without limitation, the enzymatic activity associated with an enzyme such as aconitase, isocitrate dehydrogenase, ketoglutarate dehydrogenase, succinate thiokinase, succinate dehydrogenase, fumarase, malate dehydrogenase, citrate synthase, 2,5-dioxovalerate dehydrogenase, 5-dehydro-4-deoxy-D-glucarate dehydrogenase, glucarate dehydratase, aldehyde dehydrogenase, glucuronolactone reductase, L-gulonolactone oxidase, 2-dehydro-3-deoxy-D-pentanoate aldolase, xylonate dehydratase, xylonolactonase, D-xylose dehydrogenase, lactate dehydrogenase, CoA-transferase, lactyl-CoA dehydratase, or acrylyl-CoA hydratase.

It is important to note that a polypeptide having a particular enzymatic activity can be a polypeptide that is either naturally-occurring or non-naturally-occurring. A naturally-occurring polypeptide is any polypeptide having an amino acid sequence as found in nature, including wild-type and polymorphic polypeptides. Such naturally-occurring polypeptides can be obtained from any species including, without limitation, mammalian, fungal, and bacterial species. A non-naturally-occurring polypeptide is any polypeptide having an amino acid sequence that is not found in nature. Thus, a non-naturally-occurring polypeptide can be a mutated version of a naturally-occurring polypeptide, or an engineered polypeptide. For example, a non-naturally-occurring polypeptide having citrate synthase activity can be a mutated version of a naturally-occurring polypeptide having citrate synthase activity that retains at least some citrate synthase activity. A polypeptide can be mutated by, for example, sequence additions, deletions, and/or substitutions.

An organic product is not a pyruvate-derived product if that product is synthesized from pyruvate requiring more than fifteen enzymatic steps. Examples of pyruvate-derived products include, without limitation, citrate, α-ketoglutarate, succinate, fumarate, malate, oxaloacetate, 2-dehydro-3-deoxy-D-xylonate, D-xylonate, D-xylonolactone, D-xylose, acrylate, acetate, ethanol, butyrate, and lactate.

For purposes of this invention, carboxylate products, which can be in a "free acid" or "salt" form, will be referred to using the salt form nomenclature. For example, lactic acid will be referred to as lactate. Thus, in this case, it will be appreciated that the term "lactate" includes lactic acid as well as lactate.

The term "nucleic acid" as used herein encompasses both RNA and DNA, including cDNA, genomic DNA, and synthetic (e.g., chemically synthesized) DNA. The nucleic acid can be double-stranded or single-stranded. Where single-stranded, the nucleic acid can be the sense strand or the antisense strand. In addition, nucleic acid can be circular or linear.

The term "exogenous" as used herein with reference to a nucleic acid molecule and a particular cell refers to any nucleic acid molecule that does not originate from that particular cell as found in nature. Thus, all non-naturally-occurring nucleic acid molecules are considered to be exogenous to a cell once introduced into the cell. It is important to note that non-naturally-occurring nucleic acid molecules can contain nucleic acid sequences or fragments of nucleic acid sequences that are found in nature provided the nucleic acid molecule as a whole does not exist in nature. For example, a nucleic acid molecule containing a genomic DNA sequence within an expression vector is considered to be a non-naturally-occurring nucleic acid molecule, and thus is considered lobe exogenous to a cell once introduced into the cell, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be a non-naturally-occurring nucleic acid molecule. It follows that genomic DNA fragments produced by PCR or restriction endonuclease treatment as well as cDNA's are considered to be non-naturally-occurring nucleic acid molecules since they exist as separate molecules not found in nature. It also follows that any nucleic acid molecule containing a promoter sequence and polypeptide-encoding sequence (e.g., cDNA or genomic DNA) in an arrangement not found in nature is considered to be a non-naturally-occurring nucleic acid molecule.

The term "endogenous" refers to genomic material that is not exogenous. Generally, endogenous genomic material develops within an organism, tissue, or cell, and is not inserted or modified by recombinant technology. Endogenous genomic material does include within its scope naturally occurring variations.

It also is important to note that a nucleic acid molecule that is naturally occurring can be exogenous to a particular cell. For example, an entire chromosome isolated from a cell of person X would be considered an exogenous nucleic acid molecule with respect to a cell of person Y once that chromosome is introduced into Y's cell.

As used herein, the phrase "genetically modified" refers to an organism whose genome has been modified, for example, by addition, substitution or deletion of genetic material. Methods for adding or deleting genetic material are known and include, but are not limited to, random mutagenesis, point mutations, including insertions, deletions and substitutions, knock-out technology, and transformation of an organism with a nucleic acid sequence using recombinant technology, including both stable and transient transformants. The yeast cells may also catabolize starch, either naturally or because of a genetic modification, and may even be genetically modified to catabolize cellulosics through the addition of, for example, fungal based cellulases.

1. Yeast Cells Having a Crabtree-Negative Phenotype

The invention provides a variety of genetically manipulated yeast cells that have a crabtree-negative phenotype. Such recombinant yeast cells can be used to produce organic products. For example, the invention provides a yeast cell that has a crabtree-negative phenotype, and contains an exogenous nucleic acid molecule that encodes a polypeptide having enzymatic activity that leads to the formation of an organic product. Such yeast cells are within the scope of the invention provided they produce the organic product. It is noted that the produced organic product can be secreted from the yeast cell, eliminating the need to disrupt the cell membrane to retrieve the organic product. Typically, the yeast cells of the invention produce the organic product with the yield being at least about 40 grams (e.g., at least about 45, 50, 55, 65, 70, 75, 80, 85, 90, or 95 grams) of organic product for every 100 grams of glucose consumed when cultured under optimal conditions for product production. When determining the yield of organic product production for a particular yeast cell, any method can be used. See, e.g, Kiers et al., $Yeast$, 14(5):459-469 (1998). It also is noted that the enzymatic activity of the encoded polypeptide can lead to the formation of the organic product in an NADH-consuming manner. In other words, the production of the organic compound can require NADH as an energy source. The term "NAD" refers to the co-factors that act as electron and hydrogen carriers in particular oxidation-reduction reactions, while the term "NADH" refers to the reduced form of NAD. Examples of organic products whose synthesis requires NADH include, without limitation, lactate, ethanol, acetate, and acrylate. Typically, the yeast cells within the scope of the invention catabolize a hexose carbon such as glucose. However, such yeast cells also can catabolize a pentose carbon (e.g., ribose, arabinose, xylose, and lyxose). In other worth, a yeast cell within the scope of the invention can either naturally utilize a pentose carbon, or can be engineered to utilize a pentose carbon. For example, a yeast cell can be given an exogenous nucleic acid molecule that encodes xylose reductase, xylitol dehydrogenase, and/or xylulokinase such that xylose can be catabolized. The yeast cells may also catabolize starch, either naturally or because of a genetic modification, and may even be genetically modified to catabolize cellulosics through the addition of, for example, fungal based cellulases.

A yeast cell having a crabtree-negative phenotype is any yeast cell that does not exhibit the crabtree effect. The term "crabtree-negative" refers to both naturally occurring and genetically modified organisms. Briefly, the crabtree effect is defined as the inhibition of oxygen consumption by a microorganism when cultured under aerobic conditions due to the presence of a high glucose concentration (e.g., 50 grams of glucose/L). In other worth, a yeast cell having a crabtree-positive phenotype continues to ferment irrespective of oxygen availability due to the presence of glucose, while a yeast cell having a crabtree-negative phenotype does not exhibit glucose mediated inhibition of oxygen consumption. Examples of yeast cells typically having a crabtree-negative phenotype include, without limitation, yeast cells from the following genera: *Kluyveromyces, Pichia Hansenulo, Candida, Trichosporon*, and *Yomodaryrna*.

As described herein, the invention provides many different types of recombinant yeast cells capable of producing a wide variety of different organic products. For example, a yeast cell can contain an exogenous nucleic acid molecule that encodes a polypeptide having lactate dehydrogenase activity such that lactate is produced. Examples of such a polypeptide include, without limitation, bovine lactate dehydrogenase, bacterial lactate dehydrogenase, and fungal lactate dehydrogenase (e.g., *K. lactis* or *K. thermotolerans* fungal lactate dehydrogenase). Again, polypeptides having enzymatic activity such as a lactate dehydrogenase activity can be naturally-occurring or non-naturally-occurring.

It is important to note that the yeast cells described herein can contain a single copy, or multiple copies (e.g., about 5, 10, 20, 35, 50, 75, 100 or 150 copies), of a particular exogenous nucleic acid molecule. For example, a yeast cell can contain about 50 copies of exogenous nucleic acid molecule X.

It also is important to note that the yeast cells described herein can contain more than one particular exogenous nucleic acid molecule. For example, a yeast cell can contain about 50 copies of exogenous nucleic acid molecule X as well as about 75 copies of exogenous nucleic acid molecule Y. In these eases, each different nucleic acid molecule can encode a different polypeptide having its own unique enzymatic activity, For example, a yeast cell can contain four different exogenous nucleic acid molecules such that acrylate is produced. In this example, such a yeast cell can contain a first exogenous nucleic acid molecule that encodes a polypeptide having lactate dehydrogenase activity, a second that encodes a polypeptide having CoA-transferase activity, a third that encodes a polypeptide having lactyl-CoA dehydratase activity, and a fourth that encodes a polypeptide having acrylyl-CoA hydratase activity. In another example, a yeast cell can contain four different exogenous nucleic acid molecules such that D-xylose is produced. Specifically, such a yeast cell can contain a first exogenous nucleic acid molecule that encodes a polypeptide having 2-dehydro-3-deoxy-D-pentanoate aldolase activity, a second that encodes a polypeptide having xylonate dehydratase activity, a third that encodes a polypeptide having xylonolactonase activity, and a fourth that encodes a polypeptide having D-xylose dehydrogenase activity. In yet another example, a yeast cell can contain six different exogenous nucleic acid molecules such that the vitamin, L-ascorbate, is produced. Specifically, such a yeast cell can contain a first exogenous nucleic acid molecules that encodes a polypeptide having 2,5-dioxovalerate dehydrogenase activity, a second that encodes a polypeptide having 5-dehydro-4-deoxy-D-glucarate dehydrogenase activity, a third that encodes a polypeptide having glucarate dehydratase activity, a fourth that encodes a polypeptide having aldehyde dehydrogenase activity, a fifth that encodes a polypeptide having glucuronolactone reductase activity, and a sixth that encodes a polypeptide having L-gulonolactone oxidase activity.

It is important to note that enzymatic polypeptides can be used such that the desired organic product is optically pure (e.g., about 90, 95, 99% pure). For example, a polypeptide having an (L)-lactate dehydrogenase activity can be used to produce (L)-lactate.

Yeast cells within the scope of the invention also can have reduced enzymatic activity such as reduced pyruvate decarboxylase and/or alcohol dehydrogenase activity. The term "reduced" as used herein with respect to a cell and a particular enzymatic activity refers to a lower level of enzymatic activity than that measured in a comparable yeast cell of the same species. Thus, a yeast cell lacking pyruvate decarboxylase activity is considered to have reduced pyruvate decarboxylase activity since most, if not all, comparable yeast cells have at least some pyruvate decarboxylase activity. Such reduced enzymatic activities can be the result of lower enzyme concentration, lower specific activity of an enzyme, or combinations thereof. Many different methods can be used to make a yeast cell having reduced enzymatic activity. For example, a yeast cell can be engineered to have a disrupted enzyme-encoding locus using common mutagenesis or knock-out technology. See, e.g., *Methods in Yeast Genetics* (1997 edition), Adams, Gottschling, Kaiser, and Stems, Cold Spring Harbor Press (1998). Alternatively, antisense technology can be used to reduce enzymatic activity. For example, a yeast cell can be engineered to contain a cDNA that encodes an antisense molecule that prevents an enzyme from being made. The term "antisense molecule" as used herein encompasses any nucleic acid molecule that contains sequences that correspond to the coding strand of an endogenous polypeptide. An antisense molecule also can have flanking sequences (e.g., regulatory sequences). Thus, antisense molecules can be ribozymes or antisense oligonucleotides. A ribozyme can have any general structure including, without limitation, hairpin, hammerhead, or axhead structures, provided the molecule cleaves RNA.

Yeast cells having a reduced enzymatic activity can be identified using any method. For example, a yeast cell having reduced pyruvate decarboxylase activity can be easily identified using common methods. See, e.g., Ulhrich, *Methods in Enzymology* 18:109-115 (1970).

2. Yeast Cells Having a Crabtree-Positive or Crabtree-Negative Phenotype

The invention also provides a variety of genetically manipulated yeast cells that need not have a crabtree-negative phenotype, i.e., such cells can be either crabtree-positive or crabtree-negative. Such recombinant yeast cells can be used to produce organic products. For example, the invention provides a yeast cell containing an exogenous nucleic acid molecule that encodes a polypeptide that promotes catabolism of a pentose carbon (e.g., ribose, arabinose, xylose, and lyxose) by the cell Specifically, a yeast cell can have an exogenous nucleic acid molecule that encodes xylose reductase, xylitol dehydrogenase, and/or xylulokinase such that xylose can be metabolized in a more efficient manner. In addition, the yeast cells capable of catabolizing a pentose carbon also can be capable of catabolizing a hexose carbon (e.g., allose, altrose, glucose, mannose, gulose, iodose, galactose, and talose) either sequentially or simultaneously. For example, a yeast cell can be engineered such that xylose and glucose are catabolized simultaneously. It is noted that yeast cells having an increased ability to catabolize a pentose carbon can be used to engineer yeast cells that can produce organic products from pentose carbon sources. This characteristic is particularly advantageous since pentose carbon sources such as xylose are generally less expensive than hexose carbon sources such as glucose. Other carbon sources that can be catabolized include, without limitation, melibiose, sucrose, fructose, raffinose, stachyose, starch (e.g., corn starch and wheat starch), and hydrolysate (e.g., corn fiber hydrolysate and other cellulosic hydrolysates).

In addition, the invention provides a yeast cell containing an exogenous nucleic acid molecule that encodes a polypeptide that promotes accumulation of acetyl-CoA in the cytoplasm of the cell. For example, a yeast cell can have an exogenous nucleic acid molecule that encodes a polypeptide having citrate lyase activity. Alternatively, a yeast cell can have an exogenous nucleic acid molecule that encodes a mitochondrial membrane polypeptide that promotes acetyl-CoA permeability across the mitochondrial membrane. It is noted that many yeast cells lacking the ability to produce ethanol cannot grow in the absence of ethanol and acetate. Typically, a yeast cell will lack the ability to produce ethanol when either pyruvate decarboxylase or alcohol dehydrogenase activity is lacking in some manner. For example, crabtree-positive yeast (e.g., *Saccharomyces*) lacking pyruvate decarboxylase activity grow poorly in the absence of ethanol and acetate. Thus, manipulation of such crabtree-positive yeast in a manner that reduces ethanol production in order to redirect the utilization of pyruvate to other organic products (e.g., lactate and acrylate) results in poor growth characteristics when ethanol and acetate are absent, particularly since crabtree-positive yeast limit cellular respiration when in the presence of glucose. As described herein, yeast cells that can promote accumulation of cytoplasmic acetyl-CoA in some manner other than that which relies on cytoplasmic acetate concentration and acetyl-CoA synthase activity can grow in the absence of ethanol and acetate even when unable to produce ethanol. It is noted that yeast cells having the ability to grow in the absence of ethanol and acetate while lacking the ability to produce ethanol can redirect the utilization of pyruvate to produce organic products other than ethanol.

Any type of yeast can contain an exogenous nucleic acid molecule that encodes a polypeptide that promotes accumulation of acetyl-CoA in the cytoplasm of the cell. For example, a yeast cell having a crabtree-negative or crabtree-positive phenotype can contain an exogenous nucleic acid molecule that encodes a polypeptide that promotes accumulation of acetyl-CoA in the cytoplasm of the cell. Typically, such yeast cells can be identified by (1) manipulating the cell that contains the exogenous nucleic acid molecule such that it lacks pyruvate decarboxylase or alcohol dehydrogenase activity, (2) determining the growth characteristics of the cell while culturing the cell in the presence of titrating amounts of a respiratory inhibitor (e.g., antimycin A, cyanide, or azide), and (3) comparing those growth characteristics to those observed for a comparable yeast cell that does not contain the exogenous nucleic acid molecule, yet that also was manipulated to lack pyruvate decarboxylase or alcohol dehydrogenase activity. Yeast cells determined to have more favorable growth characteristics due to the presence of the exogenous nucleic acid molecule by such a comparison are considered to contain an exogenous nucleic acid molecule that encodes a polypeptide that promotes accumulation of acetyl-CoA in the cytoplasm of the cell.

Yeast cells containing an exogenous nucleic acid molecule that encodes a polypeptide that promotes accumulation of acetyl-CoA in the cytoplasm of the cell also can have reduced enzymatic activity, such as reduced pyruvate decarboxylase and/or alcohol dehydrogenase activity. For example, a yeast cell can lack the ability to produce ethanol. Typically, such yeast cells have a growth rate under culture conditions lacking ethanol and acetate that is greater (e.g., about 5, 10, 20, 35, 50, 75, 100, 150, 200 percent, or more) than the growth rate observed for comparable yeast cells (i.e., yeast cells lacking the ability to produce ethanol) that do not contain the exogenous nucleic acid, yet were cultured under similar conditions (i.e., culture conditions lacking ethanol and acetate).

The invention also provides a yeast cell having reduced activity of a polypeptide. Such yeast cells can have a crabtree-positive or crabtree-negative phenotype. For example, a yeast cell within the scope of the invention can have reduced activity of a plasma membrane polypeptide (e.g., a plasma membrane transporter), a cytoplasmic polypeptide (e.g., pyruvate decarboxylase), and/or a mitochondrial polypeptide (e.g., pyruvate dehydrogenase). The term "plasma membrane transporter" refers to polypeptides that facilitate the movement of organic products across the plasma membrane. Examples of such a polypeptide include, without limitation, carboxylic acid transporters such as JEN1 in *S. cerevisiae* (Genbank accession number U24155). The term "mytochondrial polypeptide" refers to any polypeptide that functions within the mitochondria including, without limitation, pyruvate dehydrogenase, polypeptides that participate in the catabolism of lactate or acetyl-CoA (e.g., cytochrome b2 polypeptides), and Krebs cycle enzymes. Krebs cycle enzymes include aconitase, isocitrate dehydrogenase, ketoglutarate dehydrogenase, succinate thiokinase, succinate dehydrogenase, fumarase, malate dehydrogenase, and citrate synthase. As described herein, a yeast cell having a reduced enzyme activity includes a yeast cell that completely lacks a particular enzymatic activity. It is important to note that the term "reduced" as used herein with respect to a yeast cell and polypeptide activity refers to a lower level of activity than that measured in a comparable yeast cell of the same species under similar conditions. Thus, a yeast cell lacking a particular transport activity is considered to have reduced transport activity if a comparable cell has at least some transport activity. Such reduced polypeptide activities can be the result of lower polypeptide concentration, lower specific activity of the polypeptide, or combinations thereof. Any of various methods can be used to make a yeast cell having reduced polypeptide activity. For example, the locus having a nucleic acid sequence that encodes a mitochondrial polypeptide can be rendered inactive by, for example, common mutagenesis or knock-out technology.

It is noted that yeast cells having reduced activity of a mitochondrial enzyme can accumulate Krebs cycle products (e.g., citrate, isocitrate, α-ketoglutarate, succinyl-CoA, succinate, fumarate, malate, and oxaloacetate). For example, yeast cells having reduced fumarase activity can accumulate fumarate. In addition, the yeast cell can contain an exogenous nucleic acid molecule that encodes a polypeptide having enzymatic activity that leads to the formation of an organic product such that the cell produces the organic product.

It is important to note that some Krebs cycle products cannot permeate the mitochondrial membrane (e.g., α-ketoglutarate and succinyl-CoA). Thus, reducing the activity of particular Krebs cycle enzymes will result in the accumulation of certain Krebs cycle products within the lumen of the mitochondria. In these cases, yeast cells having a reduced activity of a Krebs cycle enzyme can be engineered to contain one or more different exogenous nucleic acid molecules, each of which encode a polypeptide having a different enzymatic activity, such that the desired Krebs cycle product accumulates within the cytoplasm. For example, reducing the activity of ketoglutarate dehydrogenase will lead to an accumulation of α-ketoglutarate, which in turn will lead to an accumulation of isocitrate. α-ketoglutarate cannot permeate the mitochondrial membrane, whereas isocitrate can permeate the mitochondrial membrane. Thus, isocitrate can accumulate within the cytoplasm of the cell. However, yeast cells that also contain an exogenous nucleic acid molecule that encodes a polypeptide having isocitrate dehydrogenase activity, and express that functional polypeptide within the cytoplasm can produce cytoplasmic α-ketoglutarate. Thus, reducing the activity of particular Krebs cycle enzymes while providing exogenous nucleic acid molecules that encode the same (or different) Krebs cycle enzymes such that they are functional within the cytoplasm can lead to the production of various Krebs cycle products (or products derived from Krebs cycle products) within the cytoplasm.

Further, the invention provides a yeast cell having reduced activity of an enzyme that diverts the utilization of a carbon source away from the production of either biomass or the desired organic product. For example, enzymes within the glycerol or certain pathways can be disrupted such that the carbon source within the culture medium is utilized predominately for the production of biomass or the desired organic product. Examples of glycerol pathway enzymes include, without limitation, dihydroxyacetone phosphate reductase. Examples of certain pathway enzymes include, without limitation, alpha-acetolactate synthase and alpha-acetolactate decarboxylase. Again, any method can be used to reduce the activity of an enzyme.

Moreover, any of the yeast cells provided herein can contain an exogenous nucleic acid molecule that functions as a killer plasmid. The term "killer plasmid" as used herein refers to a nucleic acid molecule that provides one species of yeast with the ability to kill another species of yeast. For example, yeast cells from the genus Kluyveromyces containing a killer plasmid can prevent the growth of yeast from the genus Saccharomyces. Thus, yeast cells having a killer plasmid can be used to prevent contamination problems that arise during large-scale production processes. In addition, any type of killer plasmid can be given to a yeast cell. For example, a killer plasmid isolated from K. thetis can be given to a K. marxianus yeast cell. Yeast cells containing a killer plasmid can be easily identified using common methods. See, e.g., Gunge et al., J. Bacteriol. 145(1):382-390 (1981); Gunge and Kitada, Eur. J. Epidemiol., 4:409-414 (1988); and Wesolowski-Louvel et al., Nonconventional yeasts in Biotechnology; Kluyveromyces lactis, ed. Klaus Wolf, Springer Verlag, Berlin, p. 138-201 (1996).

Likewise, any of the yeast cells provided herein can contain an exogenous nucleic acid molecule that encodes a polypeptide having an ATPase activity modified such that the yeast cell becomes more tolerant to low pH environments. For example, a yeast cell can be given an ATPase that effectively maintains a low cytoplasmic proton concentration when the extracellular proton concentration is high. Such polypeptides can be engineered as described by Morsomme et al. (EMBO J. 15:5513-5526 (1996)).

It is important to note that any of the recombinant yeast cells described herein can contain any combination of the described genetic manipulations. For example, a yeast cell having a crabtree-positive phenotype can contain an exogenous nucleic acid molecule that encodes a polypeptide having citrate lyase activity as well as an exogenous nucleic acid molecule that encodes a polypeptide having enzymatic activity that leads to the formation of an organic product.

3. Suitable Organisms

A variety of organisms are suitable for use in accordance with the invention. In addition to crabtree negative and crabtree positive yeast microorganisms such as Saccharomyces sp., including S. cerevisiae and S. uvarum, Kluyveromyces, including K. thermotolerans, K. lactis, and K. marxianus, Pichia, Hansenula, including H. polymorpha, Candidia, Trichosporon, Yamadazyma, including Y. stypitisk, or Torulaspora pretoriensis, organisms from a wide array of microbial species could also serve as hosts for lactic acid production. For example, an organism such as Rhizopus oryzac, a natural producer of lactic acid, could be genetically modified for acid tolerance, yield improvement, and optically pure lactic acid. Aspergillus spp. are also known to produce a variety of organic acids, such as citric acid, and tolerate low pH. Methods for genetically modifying Aspergillus spp. to produce lactic acid are available. Moreover, fungi such as Rhizopus and Aspergillus spp. produce enzymes that enable them to degrade starch and other carbohydrate polymers to monomer carbohydrates for use as a carbon source.

Prokaryotes such as Escherichia coli, Zymomonas mobilis, and Bacillus spp. have been or can be genetically modified for lactic acid production. Microorganisms that have been identified as Bacillus coagulans are also natural producers of lactic acid that could be further genetically modified to improve low pH lactic acid production. Additionally, extremeophile organisms from the family Archea can tolerate extremely low pH and high temperatures. Genetic modification of selected species from this family could provide a lactic acid producing strain.

4. Genetic Aspects

A nucleic acid molecule encoding a polypeptide having enzymatic activity can be identified and obtained using any method. For example, standard nucleic acid sequencing techniques and software programs that translate nucleic acid sequences into amino acid sequences based on the genetic code can be used to determine whether or not a particular nucleic acid has any sequence homology with known enzymatic polypeptides. Sequence alignment software such as MEGALIGN® (DNASTAR, Madison, Wis., 1997) can be used to compare various sequences. In addition, nucleic acid molecules encoding known enzymatic polypeptides can be mutated using common molecular cloning techniques (e.g., site-directed mutagenesis). Possible mutations include, without limitation, deletions, insertions, and base substitutions, as well as combinations of deletions, insertions, and base substitutions. Further, nucleic acid and amino acid databases (e.g., GenBank®) can be used to identify a nucleic acid sequence that encodes a polypeptide having enzymatic activity. Briefly, any amino acid sequence having some homology to a polypeptide having enzymatic activity, or any nucleic acid sequence having some homology to a sequence encoding a polypeptide having enzymatic activity can be used as a query to search GenBank®. The identified polypeptides then can be analyzed to determine whether or not they exhibit enzymatic activity.

Nucleic acid molecules that encode a polypeptide having enzymatic activity can be identified and obtained using common molecular cloning or chemical nucleic acid synthesis procedures and techniques, including PCR. PCR refers to a procedure or technique in which target nucleic acid is amplified in a manner similar to that described in U.S. Pat. No. 4,683,195, and subsequent modifications of the procedure described therein. Generally, sequence information from the ends of the region of interest or beyond are used to design oligonucleotide primers that are identical or similar in sequence to opposite strands of a potential template to be amplified. Using PCR, a nucleic acid sequence can be amplified from RNA or DNA. For example, a nucleic acid sequence can be isolated by PCR amplification from total cellular RNA, total genomic DNA, and cDNA as well as from bacteriophage sequences, plasmid sequences, viral sequences, and the like. When using RNA as a source of template, reverse transcriptase can be used to synthesize complimentary DNA strands.

Further, nucleic acid hybridization techniques can be used to identify and obtain a nucleic acid molecule that encodes a polypeptide having enzymatic activity. Briefly, any nucleic acid molecule that encodes a known enzymatic polypeptide, or fragment thereof can be used as a probe to identify a similar nucleic acid molecules by hybridization under conditions of moderate to high stringency. Such similar nucleic acid molecules then can be isolated, sequenced, and analyzed to determine whether the encoded polypeptide has enzymatic activity.

Hybridization can be done by Southern or Northern analysis to identify a DNA or RNA sequence, respectively, which hybridizes to a probe. The probe can be labeled with a radioisotope such as $^{32}P$, an enzyme, digoxygenin, or by biotinylation. The DNA or RNA to be analyzed can be electrophoretically separated on an agarose or polyacrylamide gel, transferred to nitrocellulose, nylon, or other suitable membrane, and hybridized with the probe using standard techniques well known in the art such as those described in sections 7.39-7.52 of Sambrook et al., (1989) *Molecular Cloning*, second edition, Cold Spring Harbor Laboratory, Plainview, N.Y. Typically, a probe is at least about 20 nucleotides in length. For example, a probe corresponding to a 20 nucleotide sequence that encodes a mammalian citrate lyase can be used to identify a nucleic acid molecule that encodes a fungal polypeptide having citric lyase activity. In addition, probes longer or shorter than 20 nucleotides can be used.

Any method can be used to introduce an exogenous nucleic acid molecule into a cell. In fact, many methods for introducing nucleic acid into yeast cells are well known to those skilled in the art. For example, transformation, electroporation, conjugation, and fusion of protoplasts are common methods for introducing nucleic acid into yeast cells. See, e.g., Ito et al., *J. Bacteriol.* 153:163-168 (1983); Durrens et al., *Curr. Genet.* 18:7-12 (1990); and Becker and Guarente, *Methods in Enzymology* 194:182-187 (1991).

It is important to note that the exogenous nucleic acid molecule contained within a yeast cell of the invention can be maintained within that cell in any form. For example, exogenous nucleic acid molecules can be integrated into the genome of the cell or maintained in an episomal state. In other words, a cell of the invention can be a stable or transient transformant. In addition, the yeast cells described herein can contain a single copy, or multiple copies (e.g., about 5, 10, 20, 35, 50, 75, 100 or 150 copies), of a particular exogenous nucleic acid molecule as described above.

Methods for expressing an amino acid sequence from an exogenous nucleic acid molecule are well known to those skilled in the art. Such methods include, without limitation, constructing a nucleic acid such that a regulatory element promotes the expression of a nucleic acid sequence that encodes a polypeptide. Typically, regulatory elements are DNA sequences that regulate the expression of other DNA sequences at the level of transcription. Thus, regulatory elements include, without limitation, promoters, enhancers, and the like. Moreover, methods for expressing a polypeptide from an exogenous nucleic acid molecule in yeast are well known to those skilled in the art. For example, nucleic acid constructs that are capable of expressing exogenous polypeptides within *Kluyveromyces* are well known. See, e.g., U.S. Pat. Nos. 4,859,596 and 4,943,529.

As described herein, yeast cells within the scope of the invention contain an exogenous nucleic acid molecule that, for example, encodes a polypeptide having enzymatic activity that leads to the formation of an organic product. Methods of identifying cells that contain exogenous nucleic acid are well known to those skilled in the art. Such methods include, without limitation, PCR and nucleic acid hybridization techniques such as Northern and Southern analysis. In some cases, immunohistochemistry and biochemical techniques can be used to determine if a cell contains a particular nucleic acid by detecting the expression of the encoded enzymatic polypeptide encoded by that particular nucleic acid molecule. For example, an antibody having specificity for an encoded enzyme can be used to determine whether or not a particular yeast cell contains that encoded enzyme. Further, biochemical techniques can be used to determine if a cell contains a particular nucleic acid molecule encoding an enzymatic polypeptide by detecting an organic product produced as a result of the expression of the enzymatic polypeptide. For example, detection of lactate after introduction of an exogenous nucleic acid molecule that encodes a polypeptide having lactate dehydrogenase activity into a yeast cell that does not normally express such a polypeptide can indicate that that yeast cell not only contains the introduced exogenous nucleic acid molecule but also expresses the encoded enzymatic polypeptide from that introduced exogenous nucleic acid molecule. Methods for detecting specific enzymatic activities or the presence of particular organic products are well known to those skilled in the art. For example, the presence of lactate can be determined as described elsewhere. See, Witte et al., *J. Basic Microbiol.* 29:707-716 (1989).

The invention also provides a nucleic acid construct containing a recombination sequence and a selected sequence. The term "recombination sequence" as used herein refers to any nucleic acid sequence that corresponds to a genomic sequence found within a cell. The recombination sequences described herein can be used to direct recombination events during the generation of knock-out organisms. In other words, a recombination sequence can be used to specifically disrupt a locus containing a nucleic acid sequence that encodes a particular enzyme. The term "selected sequence" as used herein includes any nucleic acid sequence. Typically, a selected sequence encodes a polypeptide having enzymatic activity that leads to the formation of an organic product within a cell. Thus, the nucleic acid constructs of the invention can be used to knockout an endogenous enzyme activity and add an exogenous enzyme activity in a single step. In most cases, the selected sequence is within the recombination sequence such that the selected sequence is flanked on each end by the recombination sequence.

5. Organic Product Production and Culturing Methods

The invention provides methods for producing organic products using any of the yeast cells or other microbial cells provided herein. Such methods involve providing yeast cells and culturing the provided yeast cells with culture medium such that an organic product (e.g., glycerol, acrylate, xylose, ascorbate, lactate, citrate, isocitrate, alpha-ketoglutarate, succinyl-CoA, succinate, fumarate, malate, and oxaloacetate) is produced. In general terms, the culture media and/or culture conditions can be classified into one of two categories: those that promote cellular respiration and/or the production of biomass and those that reduce cellular respiration. Typically, culture media and/or culture conditions that promote cellular respiration are used in situations where rapid growth is needed, or where the organic product to be produced cannot be produced without cellular respiration. Such organic products can include, without limitation, Krebs cycle products. On the other hand, culture medium and/or culture conditions that reduce cellular respiration are used in situations where rapid growth is not needed or not desired, or where the organic product to be produced can be produced without cellular respiration. Such organic products include, without limitation, lactate, acrylate, and xylose.

As used herein, the phrase "promote cellular respiration" or "promote biomass production" when referring to a culture conditions, means that the cell culture conditions are maintained such that the carbon source within the culture medium is predominantly metabolized by oxidative respiration or to produce biomass. As used herein, the term "biomass" refers to the dry weight of the organism. As used herein, the phrase "predominantly metabolized to produce biomass" means that at least about 0.3 grams biomass is produced per gram carbon source (in the form of carbohydrate) consumed (e.g., at least about 0.4, 0.45, 0.5 or 0.6 grams biomass). Generally, between about 0.3 to about 0.6 grams biomass is produced per gram carbon source. Methods for determining the amount of biomass (cell dry weight) in a culture are known and include, for example, the methods described by Postma et al., "Enzymic analysis of the Crabtree effect in glucose-limited chemostat cultures of *Saccharomyces cerevisiae*," *Appl. Environ. Microbiol.* 53, 468-477 (1989); and Kliers et al., "Regulation of alcoholic fermentation in batch and chemostat cultures of *Kluyveromyces lactis* CBS 2359," *Yeast*, 14, 459-469 (1998). Methods for determining the amount of carbon source consumed are known, and include, for example HPLC methodologies.

It should be noted that the efficiency of carbon source utilization may depend on the carbon source and the organism. Thus, while a complex growth media that includes carbon sources other than carbohydrate may be used, the amount of biomass produced per gram carbon source refers only to the amount of biomass produced per gram carbohydrate carbon source consumed.

In general, culture medium containing an inhibitor of cellular respiration (e.g., antimycin A, cyanide, and aside) can reduce cellular respiration, while the absence of such inhibitors can promote cellular respiration. Likewise, anaerobic culture conditions can reduce cellular respiration, while aerobic culture conditions can promote cellular respiration. An aerobic condition is any condition where oxygen is introduced or occurs naturally and serves as a substrate for the respiratory pathway. Generally, the term "aerobic" refers to a culture condition in which the culture media is maintained under an air flow of at least 0.1 VVM (volume air/volume liquid/minute) (e.g., greater than 0.2, 0.3, 0.4, 0.5, 1.0, 1.5 or 2.0 VVM). If a gas other than air is used then the nominal VVM is adjusted to an air equivalent based on oxygen content of the gas. Alternately, "aerobic" can be defined as a culture media that has a dissolved oxygen content of at least 2 percent (e.g., at least 5, 10, 20, 30, 40, 50, 60, 75 or 80 percent) relative to the amount present at saturated conditions with air at atmospheric pressure.

An anaerobic condition is any condition where oxygen is purposely or naturally made essentially unavailable to the respiratory pathway, leading to, for example, the production of a reduced product such a ethanol. Generally, a condition where culture medium has a dissolved oxygen (DO) content less than about 2.0% (e.g., less than about 1.5, 1.0, or 0.5%, or equal to about 0%) is considered an anaerobic condition. Likewise, a condition having a VVM (volume air/volume liquid/minute) less than about 0.1 (e.g., less then about 0.05, or equal to about 0) is considered an anaerobic condition. Typically, the term "air" as used herein with respect to VVM refers to air as it exists in the atmosphere. Other culture conditions that can influence cellular respiration include, without limitation, pH, temperature, and the presence of particular carbon sources (e.g., glucose). it is important to note that some culture media and/or culture conditions that promote cellular respiration within one species of yeast can reduce cellular respiration within another species. For example, the presence of glucose within culture medium reduces cellular respiration in yeast cells having a crabtree-positive phenotype while having little or no effect on cellular respiration in yeast cells having a crabtree-negative phenotype.

Directed manipulation of culture conditions during a commercial production can be an important step in achieving optimal levels of a desired organic product as described herein. Typically, a yeast cell within the scope of the invention is grown under culture conditions that promote cellular respiration to produce a significant cell density. For example, yeast cells can be placed into a culture vessel, and given an abundance of glucose and oxygen. Typically, under conditions that promote cellular respiration, the doubling time for the microorganisms provided herein is less than about 10 hours (e.g., less than about 8, 5, or 3 hours). Once the cells reach a significant density, the culture conditions can be switched to conditions that reduce cellular respiration such that an organic product not requiring cellular respiration is produced. For example, the yeast cells can be transferred to a culture vessel and given an abundance of glucose, but no oxygen. In this case, directly manipulating the culture conditions such that they are switched from aerobic to anaerobic can produce optimal levels of a desired organic product. Alternatively, in some cases, the cells can be cultured solely under conditions that promote cellular respiration such that an organic product requiring cellular respiration is produced. It is noted that the cell mass within the production vessel typically is greater than about 2 g/L (e.g., greater than about 4, 6, or 8 g/L).

During culturing, the temperature can be greater than about 35° C. (e.g., greater than about 36, 37, 38, 39, 40, 41, 42, 43, 44, or 45° C.). In addition, the culture medium can be liquid. The culture media typically contains a carbon source. Generally, the carbon source includes carbohydrate containing raw materials. Typically, the nutrient media also contains a nitrogen source. Preferably the nitrogen source includes a combination of organic and inorganic nitrogenous compounds.

In one mode of operation, it may be desired to fill a large fermentation vessel with a culture medium including all of the nutrients required and all of the carbohydrate, sufficient both for biomass production and for the production of the desired product. The vessel can be operated under conditions such that biomass production is promoted initially, for example, by providing aerobic conditions, and then switched to anaerobic conditions for the production of the desired product.

In an alternate mode of operation, a smaller vessel is used for biomass production, with a high level of nutrients and sufficient carbohydrate to produce, for example, about 100 g/L biomass. The contents of this vessel can then be transferred to a larger vessel, containing a second culture media that contains less nutrients, for example, only glucose as a carbon source or other carbohydrate carbon source in water. This vessel may be operate under anaerobic conditions for the production of the desired organic product. Biomass growth is reduced due to the reduced level of nutrients and the anaerobic conditions.

In a preferred embodiment, the nutrient media is kept to only the required materials in order to simplify recovery of the desired product. Use of aerobic growth can allow a simplified media to be used, relative to that needed if growth under anaerobic conditions was needed. Many of the yeast described herein can be grown, under aerobic conditions, on a media consisting only of sugar, an inorganic nitrogen source, trace minerals, and some vitamins.

Before addition of organic product to the culture medium as a result of fermentation or other processes, the culture medium generally has a pH between about 5.0 and 7.0. However, as organic products such as organic acids are secreted into the culture medium by the microorganism, the pH of the culture medium tends to decrease. The term "organic pH" as used herein refers to the pH of the culture medium attributed to organic compounds present in the medium such as carboxylates, for example, lactic acid. The term "inorganic pH" as used herein refers to the pH attributed to inorganic compounds such as HCl and $H_2SO_4$. The culture medium can have an organic pH value less than about 3.0 (e.g., less than about 2.9, 2.8, 2.7, 2.6, 2.5, 2.4, 2.3, 2.2, 2.1, 2.0, 1.9, 1.8, 1.7, 1.6, or 1.5), or an inorganic pH value less than about 3.0 (e.g., less than about 2.9, 2.8, 2.7, 2.6, 2.5, 2.4, 2.3, 2.2, 2.1, 2.0, 1.9, 1.8, 1.7, 1.6, or 1.5). Any carbon source can be used during the culturing procedure. For example, medium containing a pentose carbon (e.g., ribose, arabinose, xylose, and lyxose) can be used. In addition, medium containing a corn fiber hydrolysate can be used. A corn fiber hydrolysate can have a pH value between 2.0 and 6.5. Typically, a corn fiber hydrolysate contains glucose, xylose, and arabinose. For example, a corn fiber hydrolysate can contain about 40 grams/L glucose, about 40 grams/L xylose, and about 20 grams/L arabinose.

For large-scale production processes, the following methods can be used. First, a large tank (e.g., a 50-, 100-, 200-, or more gallon tank) containing appropriate culture medium with, for example, hexose and/or pentose carbons is inoculated with a particular microorganism. After inoculation, the culture conditions can be manipulated such that the carbon source is used predominately to produce biomass. For example, the culture medium can be manipulated to have a pH value of about 7.0, a temperature of about 35° C., and a dissolved oxygen content that creates an aerobic environment throughout the tank. It is noted that the desired organic product can be produced during this biomass production phase. Once a sufficient biomass is reached, the broth containing the microorganisms can be transferred to a second tank. This second tank can be any size. For example, the second tank can be larger, smaller, or the same size as the first tank. Typically, the second tank is larger than the first such that additional culture medium can be added to the broth from the first tank. In addition, the culture medium within this second tank can be the same as, or different from, that used in the first tank. For example, the first tank can contain medium with xylose and arabinose, while the second tank contains medium with glucose.

Once transferred, the culture conditions within the second tank can be manipulated such that the carbon source is used predominately to produce organic product wherein "organic product" includes, among other things, pyruvate-derived products and carbon dioxide ($CO_2$) but does not includes biomass (i.e., cell dry weight). As used herein, the phrase "predominantly produce a "selected organic product" or a "selected pyruvate-derived product" when referring to a culture conditions, means that the carbon source within the culture medium is metabolized, typically by a fermentation process (although not necessarily), to form at least 0.5 grams organic product per gram carbon source consumed (e.g., at least 0.6, 0.75 or 0.8 grams organic product). Methods for determining the amount of organic product produced and/or carbon source consumed are known and include, for example, HPLC.

As described earlier, the efficiency of carbon source utilization may vary depending on the substrate and organism. Thus, while a complex growth media which includes carbon sources other than carbohydrate (e.g., amino acids) may be used, the amount of organic product or pyruvate-derived product produced per gram carbon source refers only to the amount of organic product or pyruvate-derived product produced per gram carbohydrate carbon source consumed. Preferably, at this stage, no more than 0.3 grams biomass per gram carbon source is produced (e.g., no more than 0.2, 0.1, or 0.05 grams biomass).

For example, the culture medium can be manipulated to have a dissolved oxygen content that creates an anaerobic environment throughout the tank, or to contain an inhibitor of cellular respiration. In addition, the culture medium can be manipulated such that a particular pH value (e.g., an acidic, neutral, or basic pH value) is maintained. Alternatively, the pH of the culture can be adjusted periodically without maintaining any particular pH value. Typically, when producing an organic acid, the pH value of the culture medium is maintained above at least about 1.5 (e.g., at least about 2.0, 2.5, 3.0, 3.5, 4.0, 4.5, 5.0, 5.5, 6.0, 6.5, or 7.0). Further, as the microorganism catabolizes the provided carbon sources, the temperature within the tank will increase. Thus, the culture medium can be manipulated such that a particular temperature is maintained. Alternatively, the temperature of the culture medium can be adjusted periodically without maintaining any particular temperature. Typically, a temperature less than about 35° C. (e.g., less than about 34, 33, 32, 31, or 30° C.) is maintained when using heat sensitive microorganisms, while a temperature less than about 45° C. (e.g., less than about 44, 43, 42, 41, 40, 39, 38, 37, 36, or 35° C.) is maintained when using heat insensitive microorganisms. It is noted that biomass can be produced during this organic product production phase. In addition, the culture conditions within the second tank can be switched from those that promote product production to those that promote biomass production, and vice versa, one or more times. For example, the culture conditions within the second tank can be anaerobic the majority of the time with brief pulses of dissolved oxygen such that aerobic conditions periodically exist.

In another method, the anaerobic culture conditions may be modified to increase the metabolic energy of the cultured microorganism, for example, by the addition of a terminal electron acceptor. As used herein, the term "metabolic energy" refers to the energy (in terms of ATP) derived by the organism from an energy source (such as a carbon source). Under some conditions, the amount of metabolic energy obtained by the organism from the metabolism of a carbon source is greater than the amount of energy obtained from the same carbon source under different conditions.

Living cells are highly ordered and must create order within themselves in order to survive and grow. To maintain order within the organism, thousands of different chemical reactions are occurring within the organism at any instant in time. For example, cells need energy for biosynthetic reactions such as DNA, RNA and protein polymerization reactions and formation of metabolic products. Cells also need energy to bring substrates into the cell, keep metabolites within the cell, maintain a proper turgor pressure and internal pH, and for motility.

Because energy cannot be created or destroyed, the cell requires an input of energy from the environment to maintain the order. Energy is generally supplied from the environment in the form of electromagnetic radiation or chemical energy. The energy obtained from the environment is harnessed by the cell used by one of two general biochemical mechanisms: substrate level phosphorylation and electron transport.

Generally, under anaerobic conditions, ATP (the "cellular currency' for energy) is produced by substrate level phosphorylation. In substrate level phosphorylation, energy is released from chemical bonds and is stored mainly in the form of ATP.

An example of substrate level formation is the conversion of glucose to pyruvate through glycolysis:

Glucose=2Pyruvate+2ATP+2$H_2$

Pyruvate can be then be converted into lactic acid:

Pyruvate+2$H_2$=Lactate

The net energy produced by the above transformation is equivalent to 2 ATP.

Pyruvate can be further processed to tricarboxylic acid (TCA) cycle and generate additional energy and hydrogen atoms:

Pyruvate+3$H_2$O=3$CO_2$+ATP+5$H_2$

The net reaction for glucose respiration:

Glucose+6$H_2$O=6$CO_2$+4ATP+12$H_2$

Thus, by substrate level phosphorylation, the complete respiration of glucose to $CO_2$ will provide a net energy equivalent of 4 ATP and 24 hydrogen atoms.

In "electron transport", the oxidation-reduction potentials of the compounds that constitute members of an "electron transport chain" are poised such that each member can be reduced by the reduced form of the preceding member. Thus, reducing power, as electrons, can flow through the chain of carrier molecules to a terminal electron acceptor such as oxygen ($O_2$), nitrate ($NO_3^-$), and fumarate. Addition of a terminal electron acceptor such as oxygen, nitrate or fumarate to a culture medium can provide the microorganism with increased metabolic energy (e.g., increased ATP production for the same amount of carbon source consumed). Oxygen is the most preferred terminal electron acceptor.

For example, if oxygen is used as a terminal electron acceptor, hydrogen can be processed through the electron transport chain and provide the cell with an additional 1.5 ATP per hydrogen atom and 3 ATP per oxygen atom. Generally, the amount of metabolic energy can be determined by measuring the ratio of the amount of oxygen consumed to the amount of glucose consumed. Table 1 presents expected maximum and minimum improvements of energy yield (moles ATP per moles glucose) when oxygen is added during production as a function of the product yield which is decreasing due to loss of pyruvate to TCA cycle (and, consequently to respiration). Maximum % improvement was calculated assuming a P/O ratio of 3 whereas minimum % improvement assumed a P/O ratio of 0.5. Table 2 shows the estimated maximum amount oxygen consumed per mole glucose consumed. Addition of oxygen can promote minimal growth that will sequester carbon to biosynthesis leaving a small amount of carbon available for respiration (and, therefore, oxygen utilization).

TABLE 1

| Product Yield (g-lactate / g-glucose) | Maximum % improvement in energy yield | Minimum % improvement in energy yield |
|---|---|---|
| 1.0 | 0% | 0% |
| 0.9 | 160% | 35% |
| 0.8 | 320% | 70% |
| 0.7 | 480% | 105% |
| 0.6 | 640% | 140% |
| 0.5 | 800% | 175% |
| 0.4 | 960% | 210% |
| 0.3 | 1120% | 245% |
| 0.2 | 1280% | 280% |

TABLE 1-continued

| Product Yield (g-lactate / g-glucose) | Maximum % improvement in energy yield | Minimum % improvement in energy yield |
|---|---|---|
| 0.1 | 1440% | 315% |
| 0.0 | 1600% | 350% |

TABLE 2

| Product Yield (g-lactate / g-glucose) | Mole oxygen per mole glucose |
|---|---|
| 1.0 | 0.0 |
| 0.9 | 0.6 |
| 0.8 | 1.1 |
| 0.7 | 1.6 |
| 0.6 | 2.1 |
| 0.5 | 2.6 |
| 0.4 | 3.1 |
| 0.3 | 3.6 |
| 0.2 | 4.1 |
| 0.1 | 4.6 |
| 0.0 | 5.1 |

Thus, to improve the metabolic energy of the microorganisms in the cell culture, oxygen can be added to the cell culture as a terminal electron acceptor. Whereas the maximum molar yield of lactic acid from glucose is 2 mole lactate per mole glucose and the molar yield of ATP from glucose is 2 mole ATP per mole glucose, addition of oxygen as a terminal electron acceptor allows some of the pyruvate to be channeled to the citric acid (TCA) cycle where it is converted to $CO_2$ and energy. Thus, supplying a terminal electron acceptor "increases the metabolic energy" of the microorganism.

Diverting pyruvate to the TCA cycle will tend to reduce the amount of other pyruvate-derived products (such as lactic acid) produced. For example, a 10% reduction in yield may result in the generation of 2.6 times more metabolic energy for the microorganism, a 20% reduction in yield may result in the generation of 4.2 times more metabolic energy for the microorganism, and a 50% reduction in yield may result in the generation of 9 times more metabolic energy for the microorganism.

It is anticipated that in the later stages of a process, when high levels of metabolic products such as lactic acid are present, that the cell may require more metabolic energy to maintain function.

Thus, it may be desirable to expose the microorganisms within an anaerobic culture medium to brief pulses of dissolved oxygen. Preferably, the brief pulse of dissolved oxygen results in the culture medium having a dissolved oxygen concentration of no greater than 0.5 percent, preferably between about 0.1 and 0.5 percent. Alternately, the growth rate or cellular maintenance of the microorganisms during anaerobic fermentation can be increased by the addition of other terminal electron acceptors such as nitrate or fumarate. The oxygen is added at a level just sufficient to increase the metabolic energy of the microorganism while maintaining productivity at a desired level. Care must be used to avoid excessive yield loss. This technique may also be used to help consume residual sugars and thereby to further simplify recovery processes.

6. Organic Product Purification Methods

Once produced, any method can be used to isolate the desired product. For example, common separation techniques can be used to remove the biomass from the broth, and common isolation procedures (e.g., extraction, distillation, and ion-exchange procedures) can be used to obtain the organic product from the microorganism-free broth. See, e.g., U.S. Pat. No. 4,275,234; U.S. Pat. No. 5,510,526; U.S. Pat. No. 5,831,122; U.S. Pat. No. 5,641,406; and International Patent Application Number WO 93/00440. In addition, the desired organic product can be isolated while it is being produced, or it can be isolated from the broth after the product production phase has been terminated. It is important to note that the culture conditions within the second tank can be manipulated such that the isolation process is improved. For example, the pH and temperature within the second tank can be manipulated such that the desired organic product precipitates out of solution, or is in a form more amenable to isolation. Specifically, the pH value of organic acids can precipitate out of solution when the pH of the broth is less than the pKa value for the organic acid. For example, the culture conditions while producing glutamic acid can be such that the pH is less than 2.19, which is the pKa value for glutamic acid. Thus, manipulating the pH, temperature, and content of the broth can facilitate organic product isolation. In addition, particular genetically manipulated yeast can be selected and/or specific culture conditions can be manipulated such that any byproducts within the broth are such that they do not interfere with the recovery of the desired organic product.

It will be appreciated that the methods and materials described herein can be adapted and used in any type of culturing process including, without limitation, the processes commonly referred to as "continuous fermentation" and "batch fermentation" processes. In addition, the microorganisms used during one production process can be recovered and reused in subsequent production processes. For example, the microorganisms can be reused multiple times to produce a desired organic product. Further, any carbon source can be used. For example, allose, altrose, glucose, mannose, gulose, iodose, galactose, talose, melibiose, sucrose, fructose, raffinose, stachyose, ribose, arabinose, xylose, lyxose, starches such as corn starch and wheat starch, and hydrolysates such as corn fiber hydrolysates and other cellulosic hydrolysates can be used as a carbon source for the production of either biomass or the desired organic product. Moreover, any medium can be used. For example, standard culture media (e.g., yeast minimal medium and YP medium (yeast extract 10 g/L, peptone broth 20 g/L)) as well as media such as corn steep water and corn steep liquor can be used.

A significant advantage of the present invention is that the preferred microorganisms, especially when grown under aerobic conditions, can utilize minimal media. The anaerobic production typically will not require additional nutrients, so the final product can be isolated from a relatively clean fermentation broth using any of a variety of separation techniques. Liquid-liquid extraction is a well known technique for the separation of organic acids from fermentation broths, and results in considerable purification. With the present invention it is believed that simpler, less costly, less energy-consuming systems may also be useful.

In one embodiment, the present invention uses genetically modified yeast having a crabtree-negative phenotype in a train-type process that induces a "switch" in the metabolic pathway after a critical cell density has been reached and at which time it is desired to dramatically increase the specific productivity of the desired organic product. A typical method for inducing the metabolic pathway switch is by moving the biomass from a highly aerated vessel to a substantially anaerobic vessel, causing oxygen starvation. It is noted that a common carbohydrate (e.g., glucose or xylose) can be used as the carbon source during both the growth phase and the production phase. The use of a genetically modified yeast cell having a crabtree-negative phenotype can be critical to the success of this embodiment. In addition, the specific productivity of the desired organic product can be critical to success. The term "specific productivity" as used herein reflects the amount of product produced and is represented as the number of grams of organic product produced per gram of biomass (dry weight) per hour, i.e., g/(g*hour). Typically, the specific productivity for organic products such as lactate and acrylate is greater than about 0.1 g/(g*hour), for example, greater than about 0.2 g/(g*hour), or greater than about 0.5 g/(g*hour). By providing a high specific productivity as described herein, the energy required for cell maintenance may be obtained via the fermentative product pathway under substantially anaerobic conditions, rather than relying on aeration to generate high amounts of energy via the respiratory pathway. It is noted that substantially anaerobic vessels are aerated at a rate of less than about 0.1 VVM. Under certain production situations, no aeration will be used. In addition, the yield (i.e., g organic product/g carbon source consumed) in this embodiment typically is greater than about 70 wt %, and is produced without the addition of carbon sources such as ethanol and acetate. In some cases, in order to achieve the specific productivity required to generate the required energy for cell maintenance, it may be necessary to enhance the pathway from glucose to pyruvate in addition to providing the necessary enzymes to produce the desired product.

In another embodiment, the train-type process can be designed such that only the highly aerated growth vessel is equipped with sterilization capability. The anaerobic production vessel is typically operated at temperatures greater than about 35° C. (e.g., greater than about 36, 37, 38, 39, 40, 41, 42, 43, 44, or 45° C.). Few wild-type yeast will be able to survive and compete with the genetically modified yeast at such temperatures as the pH drops during product production, especially since they will not have an enhanced fermentation pathway that can generate energy for cell maintenance, in addition, the yeast can be engineered to contain "killer plasmids" as described herein, which can prevent yeast from other species from surviving. The invention also provides various methods for culturing yeast cells. For example, a yeast cell having a crabtree-negative phenotype can be cultured with culture medium either having an organic ph value less than about 3.0, or containing a corn fiber hydrolysate. Other methods for culturing yeast cells include, without limitation, culturing yeast cells having a crabtree-negative phenotype at a temperature greater than about 35° C. with culture medium either having an inorganic pH value less than about 3.0, or containing a pentose carbon or corn fiber hydrolysate.

Further, the invention provides a process for making an organic product. This process includes growing a microorganism under culture conditions, and changing the culture conditions to promote production of the organic product. In this process, the microorganism has reduced pyruvate decarboxylase, alcohol dehydrogenase, aldehyde dehydrogenase, and/or acetyl-CoA synthase activity, and exhibits a growth rate in the absence of ethanol and acetate that is at least about 30 percent (e.g., about 35, 40, 50, 75, 100, 150, 200 percent, or more) of that observed in a corresponding microorganism not having reduced pyruvate decarboxylase, alcohol dehydrogenase, aldehyde dehydrogenase, and/or acetyl-CoA synthase activity. Typically, culture conditions that promote cellular respiration are used in situations where rapid growth is needed, or where the organic product to be produced cannot be produced without cellular respiration, while culture conditions that reduce cellular respiration are used in situations where rapid growth is not needed, or where the organic product to be produced can be produced without cellular respiration.

The invention will be further described in the following examples, which do not limit the scope of the invention described in the claims.

EXAMPLES

Example 1

Figure 2:
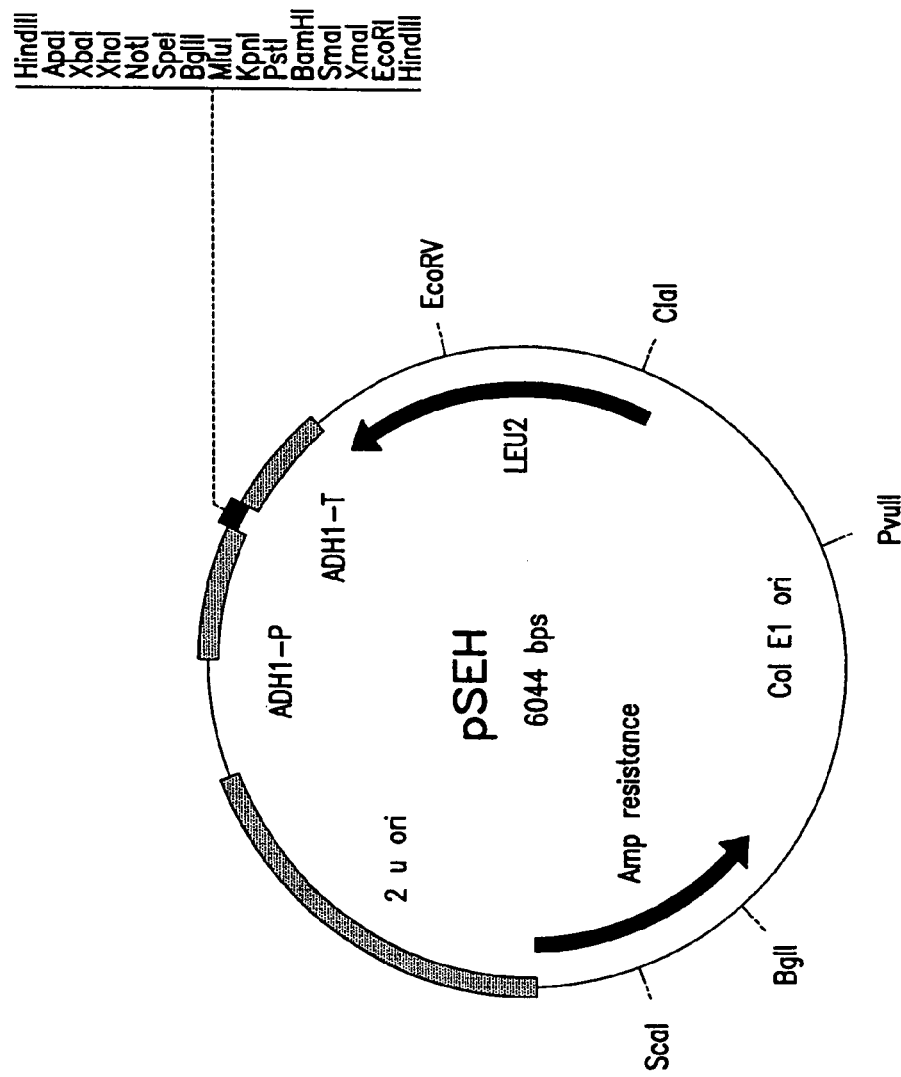
FIG. 2 is a diagram depicting the pSEH plasmid.

Recombinant Plasmid pHES/pSEH 0.5 μg of plasmid pGAD424 described by Chien et al. (*Proc. Natl. Acad. Sci.*, 88(21):9578-9582 (1991)) was digested with the restriction enzyme HindIII. The digested mixture was separated by gel electrophoresis on a 0.8% agarose gel using TBE buffer. A 5.9 kbp fragment was then purified from the gel as described in Sambrook et al., (Molecular Cloning, second edition, Cold Spring Harbor Laboratory, Plainview, N.Y. (1989)). A complementary pair of 92 bp synthetic oligomers with multiple restriction enzyme recognition sites was designed. The first was designated fwd hes oligo and has the sequence identified as SEQ ID NO: 1. The second was designated camp hes oligo and has the sequence identified as SEQ ID NO: 2. 500 nmoles of the two complementary oligomers were annealed to each other by boiling for ten minutes and cooling gradually to room temperature. The double stranded 92 bp DNA was digested with HindIII and ligated to the HindIII digested 5.9 kbp pGAD424. The ligation mixture was used to transform *E. coli* DH10B (electromax cells, Life Technologies, Rockville, Md.) by electroporation as described in Sambrook et al. (Molecular Cloning, second edition, Cold Spring Harbor Laboratory, Plainview, N.Y. (1989)). Recombinant *E. coli* was plated on Luria-Bertani broth plates, and cells containing plasmid were selected using 100 μg/ml of the antibiotic ampicillin. The plasmid DNA from ampicillin resistant *E. coli* clones were screened to obtain the two plasmids pHES and pSEH (FIGS. 1 and 2). The two plasmids differ in the orientation of the synthetic oligomer with respect to the alcohol dehydrogenase—ADH1 promoter on the vector.

Example 2

PCR Amplification of Nucleic Acid Encoding Lactate Dehydrogenase from *Lactobacillus helveticus* and *Pediococcus acidilactici*

Genomic DNA was isolated from overnight cultures of *Lactobacillus helveticus* (ATCC 10797) and *Pediococcus acidilactici* (ATCC 25741) using PUREGENE® genomic DNA isolation kit (Gentra systems, Minneapolis, Minn.). PCR primers were designed to isolate lactate dehydrogenase-encoding nucleic acid from *L. helveticus* (lh-ldh oligos) and *P. acidilactici* (pa-ldh oligos) genomic DNA. These primers were designed based on the available gene sequences for lactate dehydrogenases in the Genbank databases, and have the sequences identified as SEQ ID NO 3, SEQ ID NO: 4, SEQ ID NO: 5 and SEQ ID NO: 6. The primers were optimized using Primer Designer software obtained from Sci-ed software (Durham, N.C.). One μmole of the genomic DNA was used along with 100 nmoles of primers. Pfu DNA polymerase (New England Biolabs) was used to PCR amplify lactate dehydrogenase (LDH) nucleic acid as described in Sambrook et al. (Molecular Cloning, second edition, Cold Spring Harbor Laboratory, Plainview, N.Y. (1989)).

A similar strategy is employed to isolate L-lactate dehydrogenase-encoding nucleic acid from genomic DNA from microorganisms such as *Bacillus* sp., for example, *Bacillus megaterium* (ATCC 6458) or *Rhizopus oryzae* (ATCC 76275) or any other lactate producing organism (including microorganisms such as fungi and bacteria and multicellular organisms such mammals) or from tissue from a lactate producing organism. Genomic DNA is isolated from a growing culture of the organism using PUREGENE® genomic DNA isolation kit (Gentra systems, Minneapolis, Minn.). Suitable PCR primers are designed to isolate the lactate dehydrogenase-encoding nucleic acid based on the LDH gene sequences for these species available from Genbank. Generally, one μmole of the genomic DNA is used along with 100 nmoles of the appropriate primers. Pfu DNA polymerase (New England Biolabs) or any other suitable DNA polymerase is used to amplify lactate dehydrogenase (LDH) nucleic acid from the respective genomic DNA using PCR technology, for example, as described in Sambrook et al. (Molecular Cloning, second edition, Cold Spring Harbor Laboratory, Plainview, N.Y. (1989)).

Alternately, lactate dehydrogenase-encoding nucleic acid is isolated from *Kluyveromyces theromotolerans* ATCC 52709, *Trichoderma Reesci* ATCC 13631, *Torulaspora pretoriensis* ATCC 36245, or any other lactate dehydrogenase producing organism using the any of the following methodologies.

1) A genomic cDNA library from one of these organisms is cloned into an standard *E. coli* expression vector such as pUC19 using standard techniques (Sambrook et al., (1989) *Molecular cloning: a laboratory manual*, $2^{nd}$ ed. Cold Spring Harbor Laboratory Press, Cold Spring Harbor, N.Y.). An *E. coli* (ldh pfl) mutant strain NZN111 (Bunch et al., (1997) "The ldhA gene encoding the fermentative lactate dehydrogenase of *Escherichia coli*," *Microbiology*, 143:187-95) is transformed with this library and the cells are grown under anaerobic conditions in M9 medium supplemented with casamino acid. Any *E. coli* that grows under these conditions encodes either a lactate dehydrogenase or is a revertant in ldh or pfl. Positives (colonies that form under the anaerobic growth conditions) are screened for LDH activity using a colorimetric assay of lactic-acid specific soft-agar overlay (LASSO) that is capable of differentiating between (L)-LDH and (D)-LDH (Witte et al. (*J. Basic Microbiol.* 29:707-716 (1989)). Plasmid DNA from clones suspected of expressing L-lactate dehydrogenase are then isolated and sequenced.

2) *K. thermotolerans* ATCC 52709, *T. reesei* ATCC 13631 and *Torulaspora pretoriensis* ATCC 36245 are all eukaryotes that produce L-lactic acid when cultured under anaerobic conditions (Wine et al. (*J. Basic Microbiol.* 29:707-716 (1989)), Thus, according to this method, at least one of these strains is grown under anaerobic conditions to induce lactate dehydrogenase enzyme activity. A cell free extracts is then obtained using standard methods and subjected to known protein purification strategies to isolate the lactate dehydrogenase enzyme. Methods for purifying lactate dehydrogenase are known (Kelly et al., (1978) "Affinity chromatography of bacterial lactate dehydrogenases," *Biochem J.*, 171(3):543-7). After the protein is purified, it is partially cleaved and sequenced to determine the amino acid sequence. This amino acid sequence is then used to design degenerate primers to isolate the gene encoding lactate dehydrogenase from the genomic DNA.

An eukaryotic LDH, such as the one isolated from *K. thermotolerans* or *Trichoderma reseei* or *Torulaspora pretoriensis*, may function better (in terms of transcriptional efficiency, translational efficiency and/or protein activity) in the yeast *K. marxianus* compared to an LDH from bacterial sources such as *Bacillus* or *Lactobacillus*.

3) Using the known eukaryotic lactate dehydrogenase gene sequences available from Genbank, degenerate primers are designed to isolate the gene for lactate dehydrogenase from genomic DNA of *K. thermotolerans* ATCC 52709, *T. reesei* ATCC 13631 or *Torulospora pretoriensis* ATCC 36245. The conserved NAD+ binding site and pyruvate binding site among LDH gene sequences is used to design degenerate primers. One µmole of genomic DNA is used along with 100 nmoles of primers. Pfu DNA polymerase (New England Biolabs), or any other suitable DNA polymerase, is used to amplify fragments of the L-lactate dehydrogenase (LDH) nucleic acid according to known PCR methods, for example, those described in Sambrook et al. (Molecular Cloning, second edition, Cold Spring Harbor Laboratory, Plainview, N.Y. (1989)).

Example 3

Cloning of *L. helveticus* and *P. acidilactici* into pCRII vector

Figure 3:
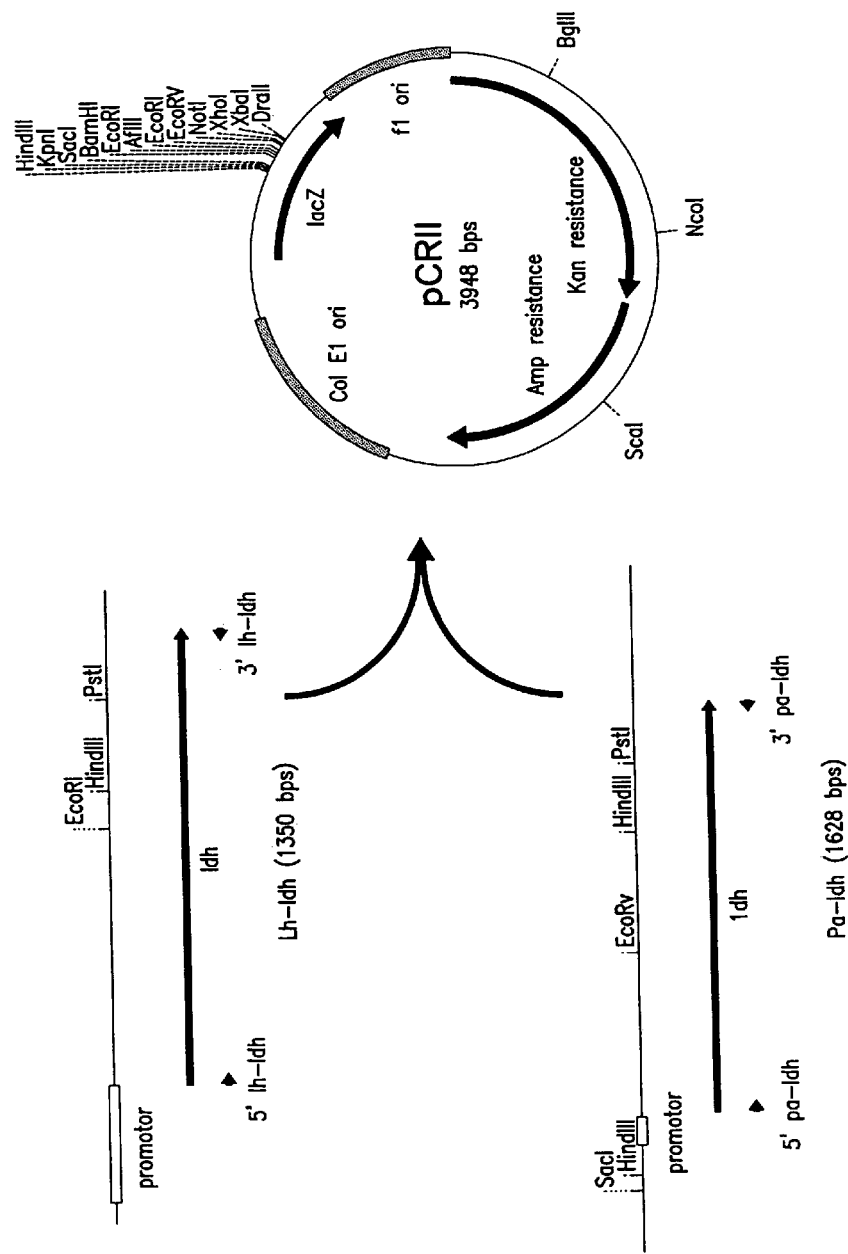
FIG. 3 is a diagram depicting the generation of pCRII plasmids containing either Lh-LDH or Pa-LDH.
Figure 4:
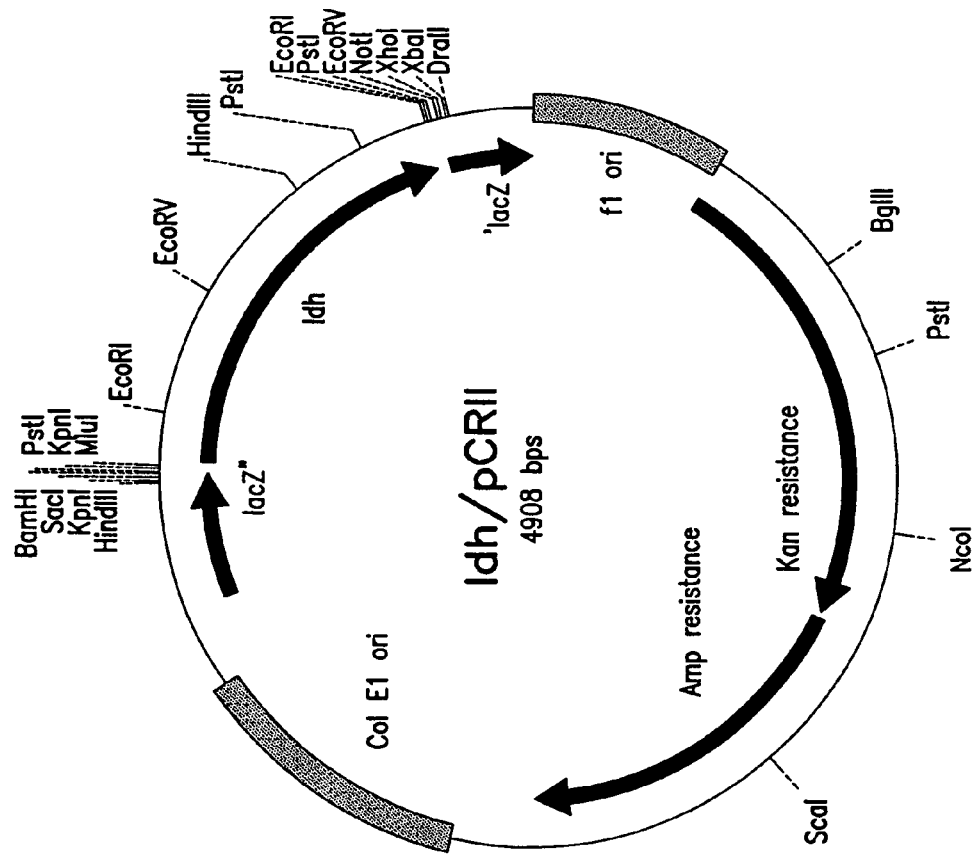
FIG. 4 is a diagram depicting the LDH/pCRII plasmids.

PCR amplified LDH DNA products were ligated with pCRII vectors (FIGS. 3 and 4) using the TA cloning kit obtained from Invitrogen (Carlsbad, Calif.). The ligation mixture was then used to transform *E. coli* DR10B using methods described in Sambrook et al. (Molecular Cloning, second edition, Cold Spring Harbor Laboratory, Plainview, N.Y. (1989)). The pCRII vectors supplied with the kit allowed for quick cloning of the PCR products according the manufacture's instructions. The pCRII vectors with the LDH genes from *L. helveticus* and *P. acidilactici* is depicted in FIG. 4.

Example 4

Figure 5:
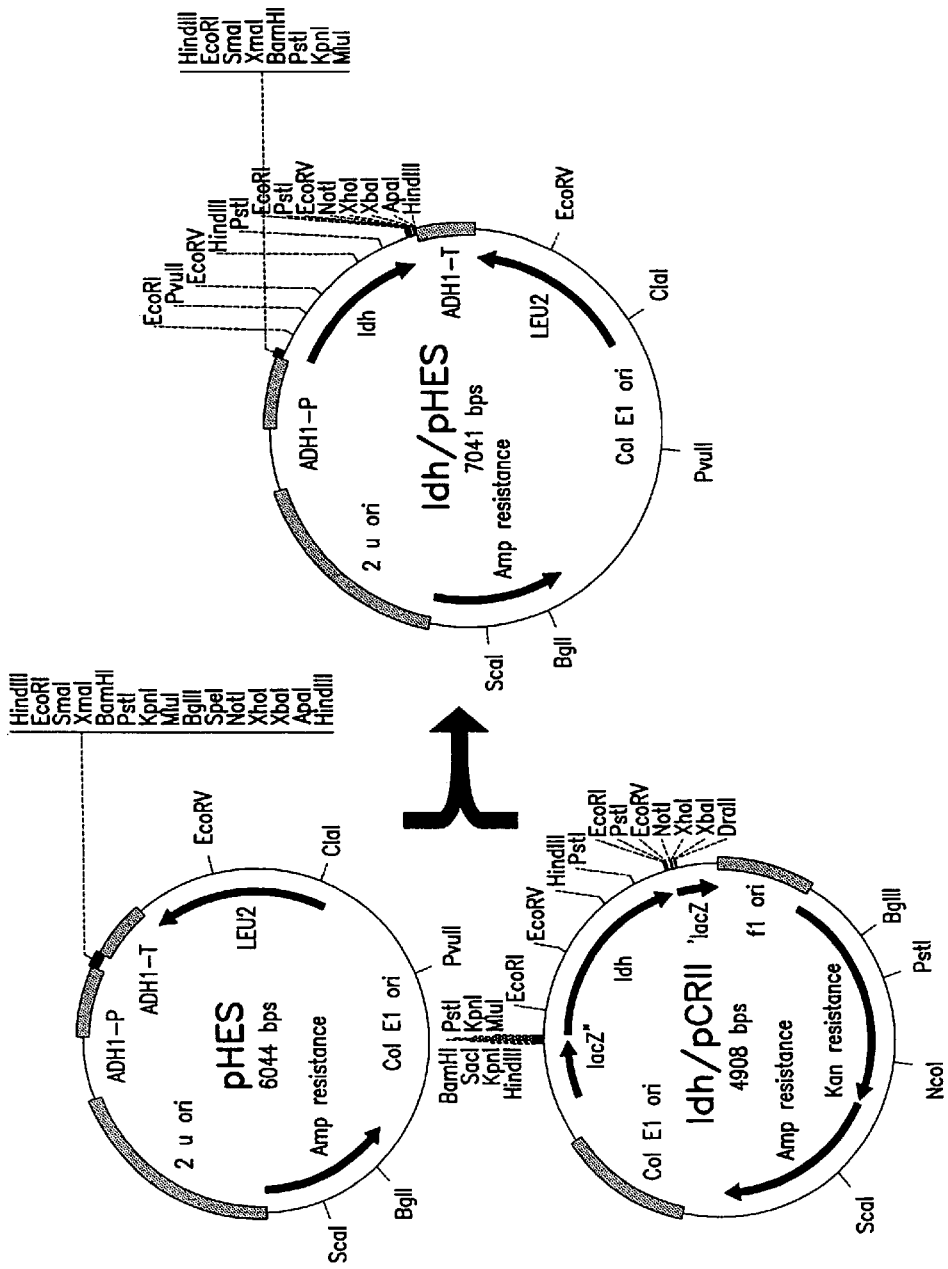
FIG. 5 is a diagram depicting the generation of pHES plasmids containing Lh-LDH or Pa-LDH.

Recombinant Plasmid pLh ldh-HES/pPa ldh-HES Having *L. Helveticus* and *P. acidilactici* LDH Genes in pHES Vector The pCRII vectors containing LDH gene from *L. helveticus* and *P. acidilactici* were digested with the appropriate restriction endonucleases. The pHES vector was similarly digested with the same restriction endonucleases. A 1 kbp insert containing LDH from pCRII vectors was then ligated to the 6.0 kbp pHES vector using T4 DNA ligase as described in Sambrook et al. (Molecular Cloning, second edition, Cold Spring Harbor Laboratory, Plainview, N.Y. (1989)). The ligation mixture was used to transform *E. coli* DH10B (electromax cells, Life Technologies, Rockville, Md.), and recombinant clones were selected for ampicillin resistance. DNA isolated from recombinant clones was analyzed to confirm the pLh ldh-HES and pPa ldh-HES vectors (FIG. 5). These vectors contain the genes encoding LDH from *L. helvecticus* and *P. acidilactici* in the pHES vector under the control of the yeast alcohol dehydrogenase promoter (ADH1).

Example 5

Cloning of *Bacillus* sp., *Rhizopus oryzae*, *K. thermotolerans*, *Trichoderma reseci* or *Torulaspora pretoriensis* LDH Gene for Expression Using the *Saccharomyces* PDC1 Gene Promoter Although it is possible to use the lactate dehydrogenase promoter found in *Rhizopus oryzae*, *K thermotolerans*, *Trichoderma reseci* or *Torulaspora pretoriensis* to control expression of a lactate dehydrogenase gene cloned in *K. marxianus*, the PDC1 promoter from *Saccharomyces cerevisiae* may be used to control expression of the isolated lactate dehydrogenase gene. *Saccharomyces cerevisiae* glycolytic promoters have been successfully used to express genes in *Kluyveromyces* strains. (Gellissen and Hollenberg, (1997) "Application of yeasts in gene expression studies: a comparison of *Saccharomyces cerevisiae*, *Hansenula polymorpha* and *Kluyveromyces lactis*—a review," Gene, 190(1):87-97).

Figure 14:
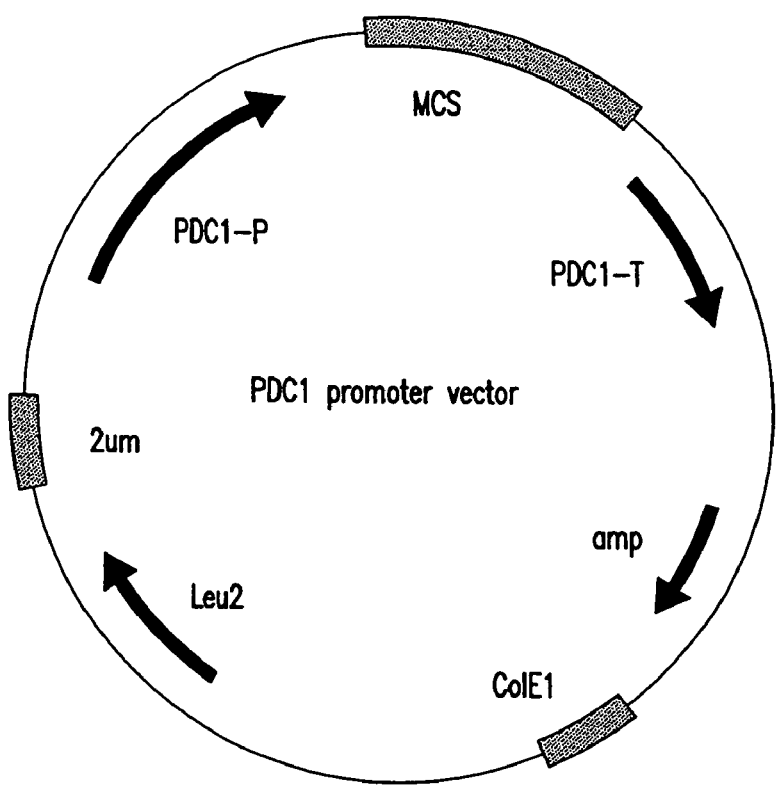
FIG. 14 is a plasmid map of PDC1 promoter vector.

Accordingly, the PDC1 promoter from *Saccharomyces cerevisiae* is obtained by designing suitable oligomeric primers using the *Saccharomyces cerevisiae* genome sequence, available in Genbank. The PDC1 gene sequence and 1 Kb regions surrounding the PDC1 gene are amplified by PCR technologies. The resulting 4 Kb DNA fragment contains both the promoter and terminators that control PDC1 gene expression. Multiple restriction enzyme sites are included between the promoter and terminators that control the PDC1 gene expression such that a variety of LDH genes can be inserted under the control of the PDCI promoter and terminators. The 4 Kb DNA fragment is inserted into a suitable vector, such as a pUC19 based *Saccharomyces cerevisiae* or *E. coli* shuttle vector. The LDH gene is then introduced into the vector at one of the multiple cloning sites under the control of the promoter and terminators such that lactate dehydrogenase gene expression is controlled by the PDC1 promoter and terminator. (FIG. 14). Alternately, other *Saccharomyces* glycolytic promoters such as those that control the expression of the *Saccharomyces cerevisiae* glyceraldehyde-3 phosphate dehydrogenase or the phosphoglycerate kinase genes may be used similarly to express the cloned LDH gene in *K. marxianus*.

Example 6

Amplification of Linear Fragments of Homologous DNA for Gene Disruptions OF Pyruvate Decarboxylase An 82 bp oligomeric primer (5' kmPDC1Ko) was designed such that it contained 51 bp identical to the 5' end of the pyruvate decarboxylase (PDC) from *K. marxianus* and 30 bp identical to the 5' end of the ADH1 promoter from pHES vectors. The sequence of 5'KmPDC1Ko is identified as SEQ ID NO: 7. The sequence for the PDC genes from yeasts (*K. marxianus* or *Y. stipitis* or *H. polymorpha*) was obtained from the submitted Genbank sequence. Similarly, a reverse 79 bp oligomer (3' kmPDC1Ko) was designed such that 54 bp were identical to the 3' end of the PDC gene and 22 bp were identical to the 3' end of the ADH1 terminator. The sequence of 3'KmPDC1Ko is identified as SEQ ID NO: 8. The primers were designed to amplify a linear DNA fragment from the pLhldh-HES and pPaldh-HES plasmids such that the fragment contains the entire lactate dehydrogenase gene along with the ADH1 promoter and terminator (FIG. 6). The PCR amplified product also contains ends that were homologous to sequences from either *K. marxianus* PDC1, *Yamadazyma stipitis* PDC1 and PDC2, and *Hansenula polymorpha* PDCI and PDC2. The amplification reaction was performed using Pfu DNA polymerase (New England Biolabs; Beverly, Mass.). 100 ng of pLhldh-HES or 5 pPaldh-HES was used in the reaction along with 5 units of polymerase and 100 nmoles of the oligomers. The reaction was carried out according to protocols described in Sambrook et al. (Molecular Cloning, second edition, Cold Spring Harbor Laboratory, Plainview, N.Y. (1989)). FIG. 6 depicts the final linear product with the described homologies.

Alternate constructs were prepared to improve the likelihood of obtaining a pdc negative strain of *K. marxianus*. To prepare these constructs, a 5.5 kbp fragment surrounding the *K. marxianus* 1.7 kbp PDC1 gene was isolated (FIG. 6b) using PCR and genome walking techniques (Clonetech). The 5.5 kbp fragment was then cloned into the pCRII TA cloning vector (Invitrogen) using standard methods. A portion of approximately 370 bp near the middle of the 1.7 kbp coding region of PDC1 was removed from the *K. marxianus* 5.5 kbp fragment by restriction digests (Sambrook). The removed fragment has the sequence identified as SEQ ID NO: 10.

Figure 6A:
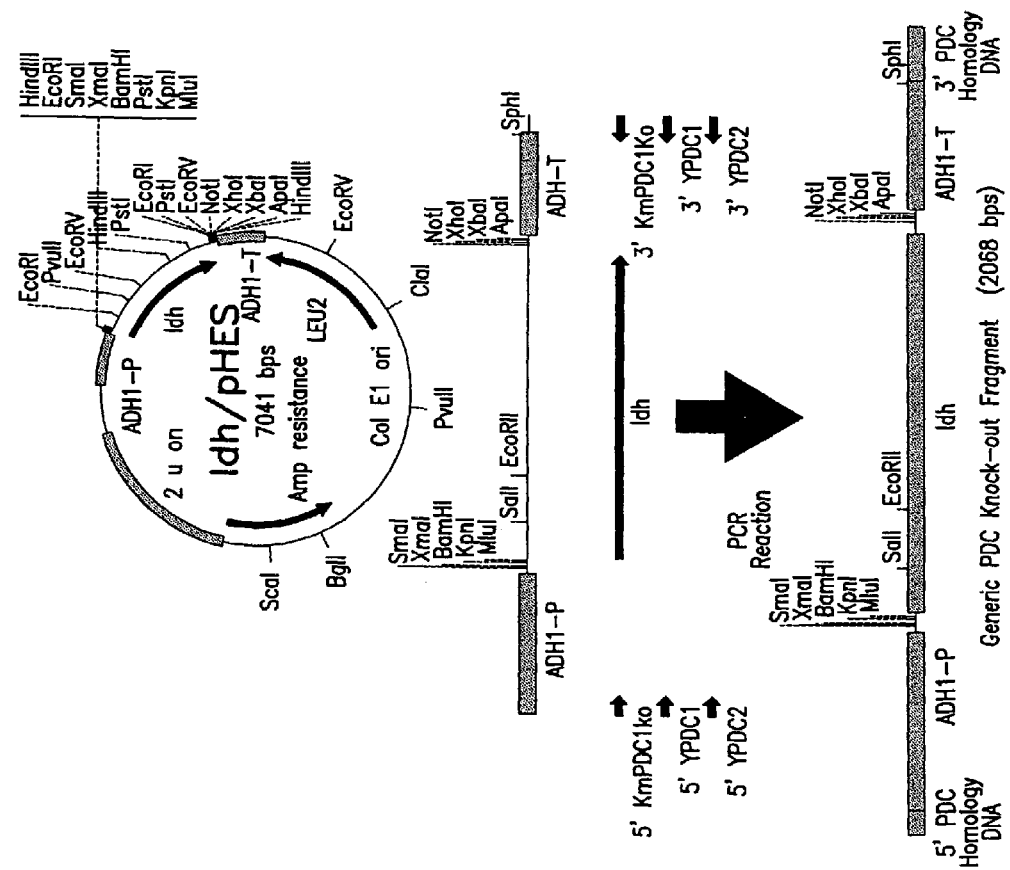
FIG. 6a is a diagram depicting the generation of pyruvate decarboxylase (PDC) knockout fragment
Figure 6B:
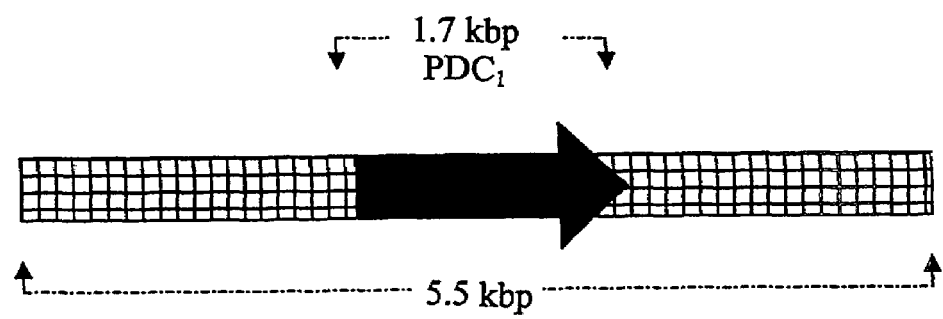
FIG. 6b is a diagram depicting the 5.5 kbp fragment surrounding the K. marxianus 1.7 kbp PDC1.
Figure 6C:
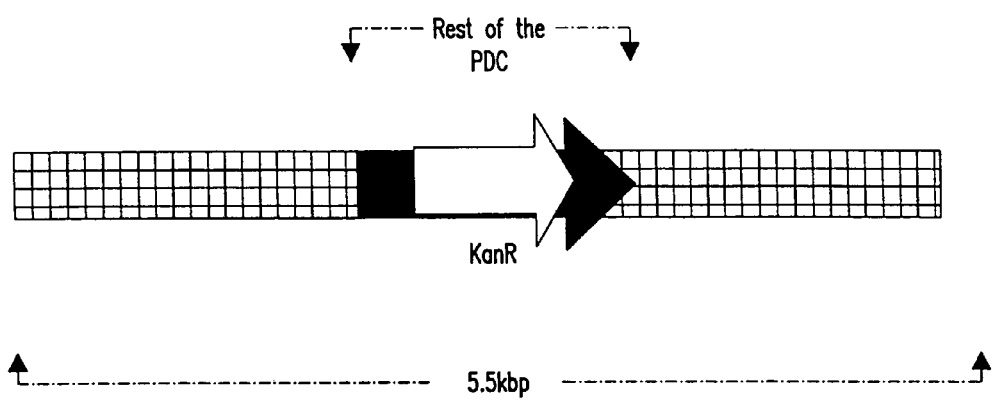
FIG. 6c is a diagram depicting the deletion of 400 bp of the 5.5 kbp PDC homologous region and the insertion of a gene for kanamycin resistance.
Figure 6D:
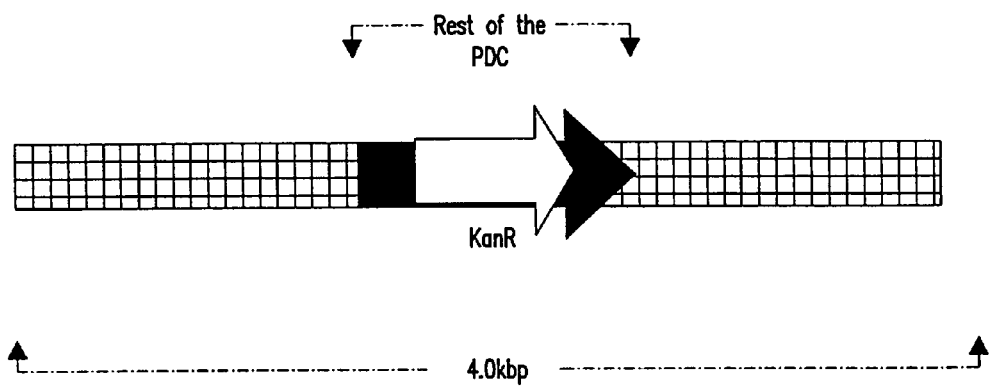
FIG. 6d is a diagram depicting the 4 kb region containing the kanamycin resistance gene and the surrounding 2.3 kbp of the PDC1.
Figure 6E:
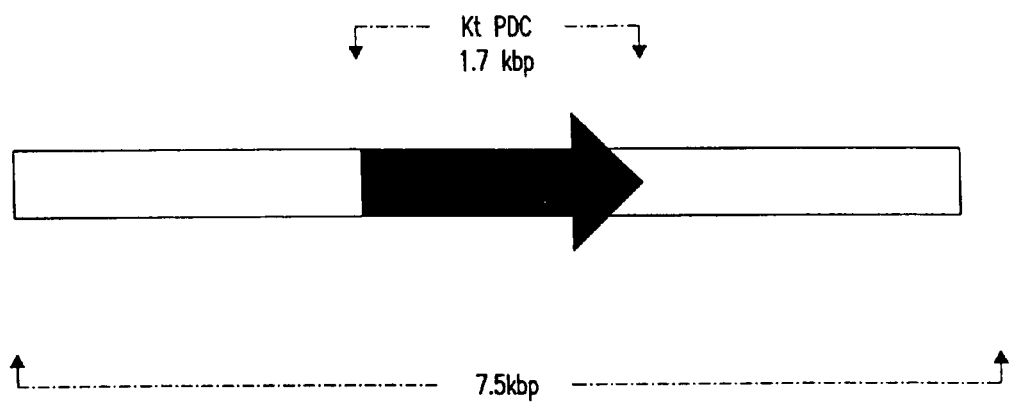
FIG. 6e is a diagram depicting the 7.5 kbp K. thermotolerans PDC1 and surrounding region.

A kanamycin resistance gene and its promoter was then isolated from a pPIC9K vector (Invitrogen) using standard restriction technology (See Sambrook et al.), and cloned into the site in the 5.5 kbp from which above-identified fragment was removed. The pPIC9K (Invitrogen) kanamycin resistance gene and its promoter were inserted such that the sequence of the inserted region was as identified as SEQ ID NO: 9. The resulting construct contains the G418 resistance gene surrounded by approximately 5 kbp of the pdc region as shown in FIG. 6c. A similar DNA construct was made which contained the internal G418 gene surrounded by 2.3 kbp of *K. marxianus* PDC1 in the pCRII vector as shown in FIG. 6d.

Example 7

Use of Linear DNA Fragment to Disrupt the Endogenous PDC Coding Sequence and Insert an LDH Coding Sequence Simultaneously The linear DNA fragment generated by PCR described in Example 5 is used to transform *K. marxianus, Yamadazyrna stipitis*, or *Hansenula polymorpha*. The protocol used for transformation is as described by Wesolowski-Louvel et al. (Nonconventional yeasts in Biotechnology: *Kluyveromyces lactis*, ed. Klaus Wolf, Springer Verlag, Berlin, p. 138-201 (1996)). Briefly, 5 ml of an overnight culture is spun down and washed with electroporation buffer (10 nM Tris-HCl, 270 nM sucrose, 1 nM $MgCl_2$, pH 7.5). The washed cells then are incubated for 30 minutes at 30° C. in incubation buffer (yeast extract 5 g/L, peptone broth 10 g/L, glucose 10 g/L, 25 nM DTT, 20 nM HEPES, pH 8.0). At the end of this period, the cells are washed again and resuspended in 400 µl incubation buffer. 200 ng of DNA is added to these cells, and the cells are pulsed using the Bio-Rad Gene Pulser at 1800 volts, 1000Ω, and 25 µF in a 0.4 cm cuvette.

The cells are plated on regular YPD (yeast extract 10 g/L, peptone broth 20 g/L, glucose 20 g/L, agar 15%) plates, and colonies are allowed to regenerate over 72 hours. Each of the plates with colonies are replica plated on fresh YPD plates and incubated for 48 hours. The colonies then are overlayed with 6.5% soft agar (0.5% agar in 300 mM Tris-HCl, 187 mM glutamate, pH 8.3). A staining mixture (3.2 ml of 1% agar, 1.6 ml of 120 mM Tris, 75 mM glutamate, pH 8.3, 0.4 ml of 2 mg/mL phenazine methosulfate, 7 units of glutamate pyruvate transaminase, and 7 units of L(+)-pig muscle lactate dehydrogenase) is added to the overlayed plates. Yeast strains with high L(+) form blue halos within 10-120 minutes, This method is similar to the method suggested by Subden et at. (*Canadian J. Microbiol.*, 28:883-886 (1982)), and modified by Witte et al. (*J. Basic Microbiol.* 29:707-716 (1989)). The colonies are selected, and the DNA isolated from the colonies is tested by PCR analysis and sequenced to detect the disrupted pyruvate decarboxylase gene.

In another embodiment, the clones described in Example 6 above and depicted in FIGS. 6c and 6d are digested with two restriction enzymes (See, Sambrook et al.) to yield approximately 3 micrograms of fragment DNA containing the homologous PDC region that includes the mid-sequence inserted kanamycin resistance gene. *K. marxianus* is transformed with the fragment using known techniques, such as electroporation, to disrupt the pdc of *K. marxianus*.

Generally, electroporation is performed as follows: a) grow a culture of the microorganism in YPAD overnight (~15 h) in a volume of 20 ml; b) transfer 500 ul from the culture to a microfuge tube, spin @4K, 4 min, discard supernatant; c) wash the pellet with 1 ml cold EB (EB=Electroporation Buffer: 10 mM Tris-HCl, pH 7.5; 270 mM Sucrose; 1 mM $MgCl_2$.); d) resuspend in 1 mL IB (IB=Incubation Buffer: YPD; 25 mM DTT; 20 mM Hepes, pH8.0.); e) shake @ 800 rpm, 30° C. for 30 min in an Eppendorf Thermomixer; f) spin down, wash once with EB, resuspend in 400 ul EB; g) add three micrograms fragment DNA (in water 10 mM Tris-Cl, pH 8.5), incubate on ice 30 min; h) transfer to 0.4 cm electroporation cuvette. Bio-Rad Gene Pulser settings: 1000V, 1000 Ω, 50 µF. Time constant after pulse: ~20 msec; i) transfer to 3 ml Morton Closure tube, incubate without shaking at 30° C. for 1 hour. Add 400 ul liquid YPAD media (YPAD: 10 g Yeast Extract; 20 g Peptone; 20 g Glucose; 100 mg Adenine Hemisulphate. Volume=1 L. No pH adjustment), shake @ 800 rpm, 30° C. for 1 hour in Eppendorf Thermomixer. Add 400 ul liquid YPAD and recover 4-6 hours; j) spin down in microfuge tube @ 4K, 4 min, discard supernatant, resuspend in 400 ul µM Sorbitol; k) plate onto 200 ug/ml G418 selective plates; and 1) incubate at 30° C. for three to five days.

The colonies are screened first by a second patching onto 300 ug/ml G418. The genomic DNA is isolated from the secondary yeast patch by standard genomic preparations (Sambrook). These are then screened via PCR for 1) the presence of the kanamycin fragment using suitable primers and conditions (Sambrook) and 2) the absence of the disrupted pdc region using suitable primers and PCR conditions. Colonies positive for the selection marker and negative for the pdc disruption region were then grown and analyzed by HPLC for physiology. Genomic DNA from those strains was further analyzed by southern hybridization analysis.

Example 8

Growth Characteristics of Cells

1. Low pH/High Temperature

Overnight cultures of *K. marxianus* were inoculated into 50 ml yeast minimal medium according to Kiers et al. (*Yeast*, 14(5):459-469 (1998)). 100 g/L glucose was used as the carbon source. The overnight cultures were maintained at 40° C., and inoculated into medium that was also maintained at 40° C. Addition of the inoculant changed the pH of the medium from 5.5 to 2.5. During the experiment, the pH remained 2.5. Glucose concentration was measured by YSI-membrane, and optical density (OD) was measured using a spectrophotometer.

Figure 7:
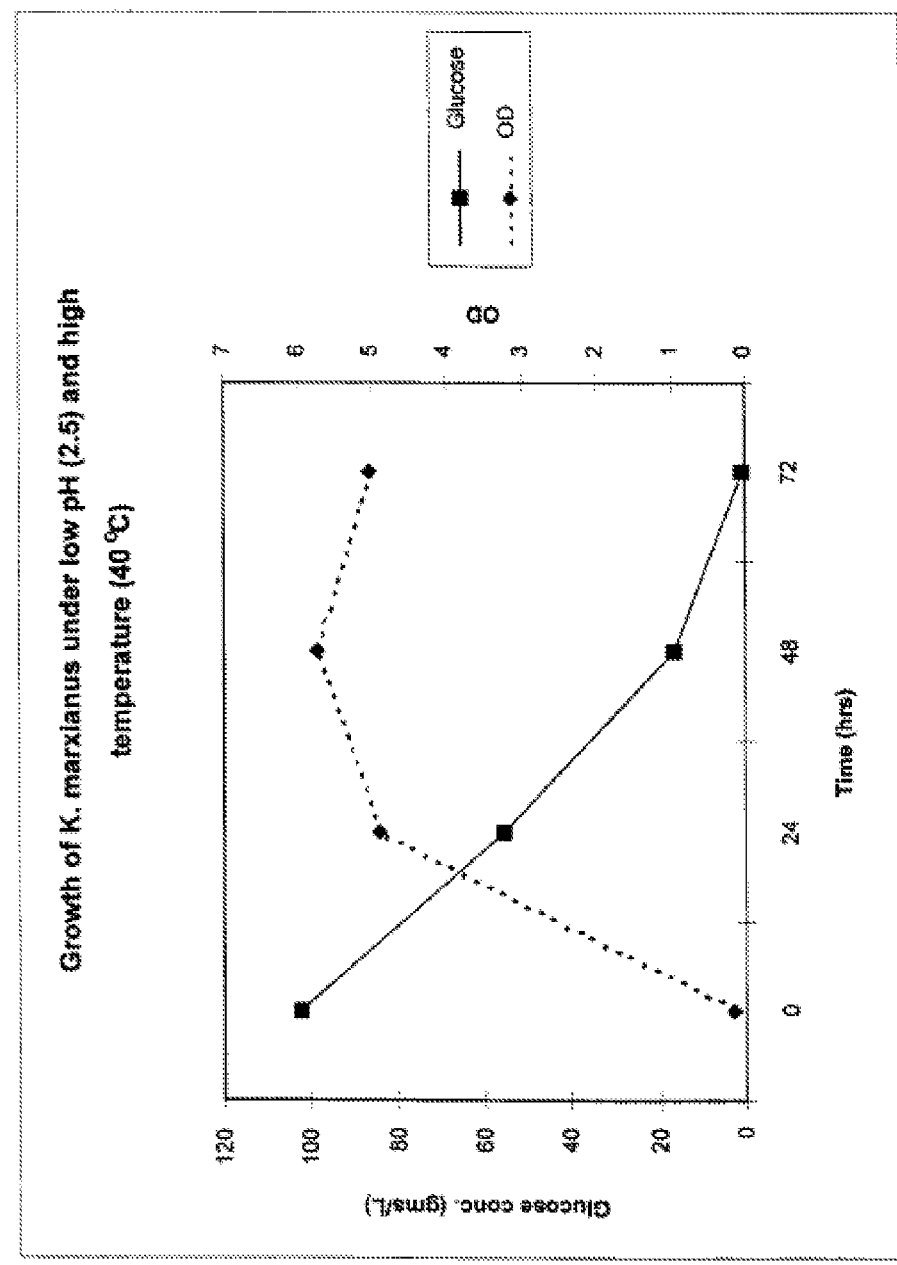
FIG. 7 is a graph plotting growth (optical density; OD) verses time (hours) for Kluyveromyces marxianus cultured under low pH (pH 2.5) and high temperature (40° C.) conditions.

Glucose was utilized in 72 hours, indicating that metabolic activity occurs under low pH and high temperature culture conditions during that time period (FIG. 7). In addition, biomass decreased slightly during the 48 to 72 time period, indicating that cell catabolism out paces anabotism (FIG. 7).

2. Pentose Carbon Sources

Overnight cultures of *K. marxianus* were inoculated into three 50 ml flasks containing yeast minimal medium according to Kiers et at. (*Yeast*, 14(5):459-469 1998)). Each of the three flasks contained a different carbon source. The first contained 10 percent glucose, the second contained 10 percent D-xylose, and the third contained 10 percent L-arabinose. The flasks were incubated at 30° C., and the OD measurements were made periodically.

Figure 8:
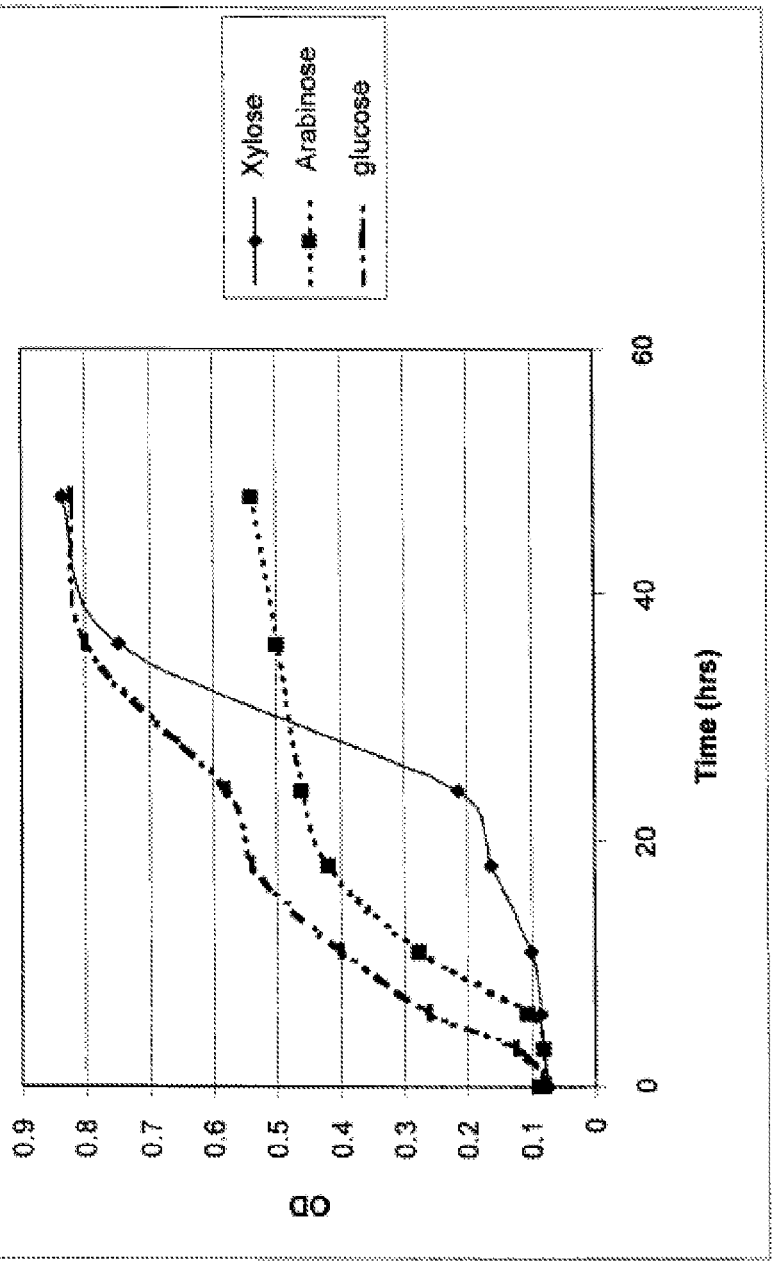
FIG. 8 is a graph plotting growth (OD) verses time (hours) for K. marxianus cultured with glucose, xylose, or arabinose at 30° C.

After 40 hours, the biomass yield for yeast cultured with glucose or xylose was similar, while the biomass yield for yeast cultured with arabinose was lower (FIG. 8). Comparing the growth of yeast cultured with glucose to those cultured with xylose or arabinose revealed an initial lag time in growth. The yeast cultured with arabinose exhibited a lag time of a few hours, while the lag time for yeast cultured with xylose was much more pronounced (FIG. 8). The presence of this lag tune indicates that the yeast cells need time to adapt to the xylose and arabinose carbon sources. Presumably, this time is needed to induce the synthesis of polypeptides not normally expressed.

3. Corn Fiber Hydrolysate at Low pH

Overnight cultures of *K. marxianus* were inoculated into flasks containing yeast minimal medium according to Kiers et al. (*Yeast*, 14(5):459-469 (1998)). Each flask contained 30% corn fiber hydrolysate as the carbon source. Briefly, the cornfiber hydrolysate was made by reacting corn fiber with 1.2% sulfuric acid at 145° C. for 25 minutes. During the reaction, the hemicellulose was broken down into the monomeric products arabinose, xylose, and glucose. Because of the high temperature during the reaction, some arabinose and xylose was degraded into furfural, while some glucose was degraded into hydroxymethylfurfural. HPLC analysis of the hydrolysate revealed the presence of 38.7 grams/L glucose, 39.1 grams/L xylose, 20.7 grams/L arabinose, and 1.6 grams/L furfural. In addition, the hydrolysate had a pH of 1.51. Before culturing the yeast the pH of the corn fiber hydrolysate was adjusted to 3.0. During the culturing experiment, OD measurements were made periodically.

Figure 9:
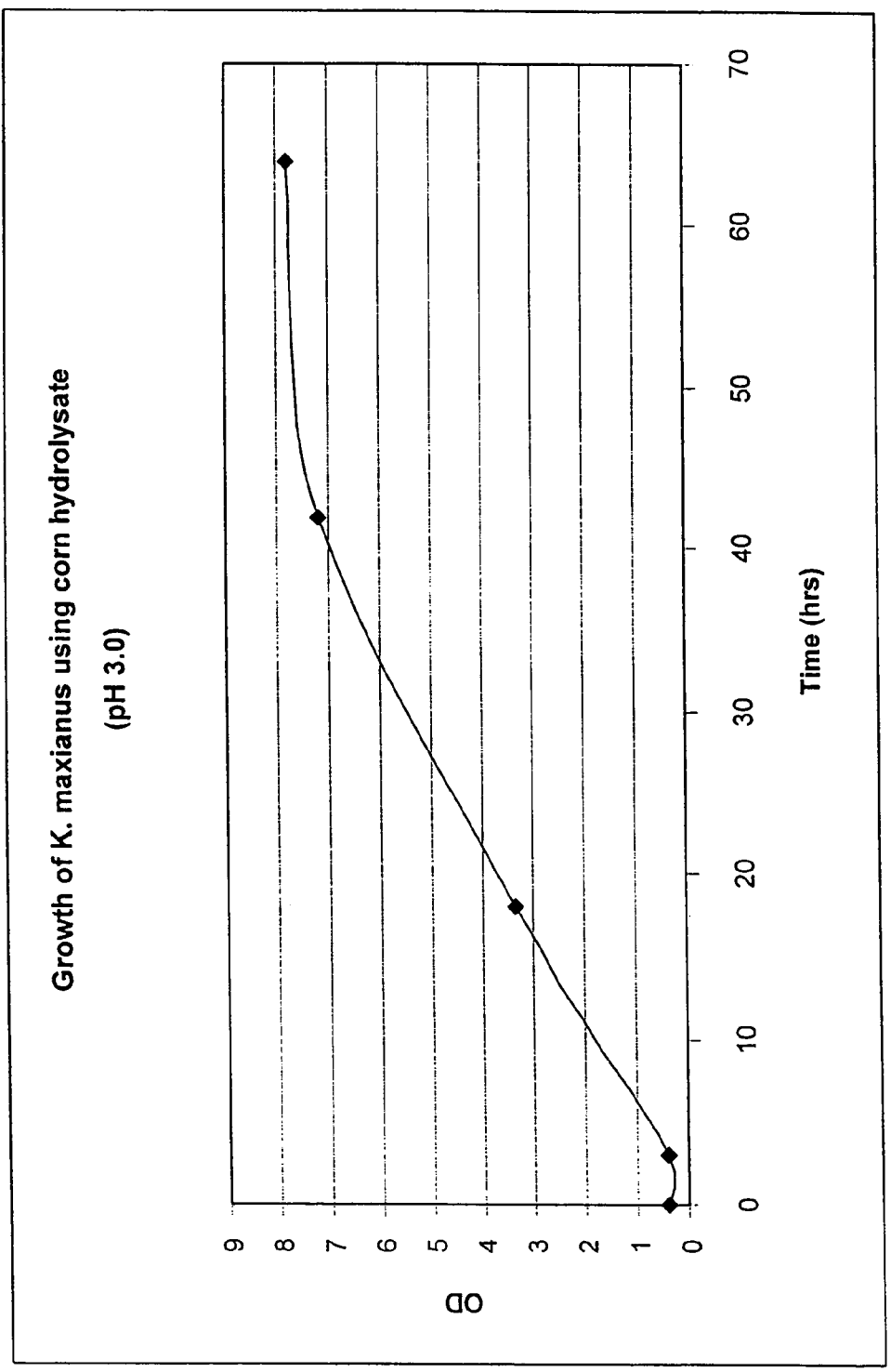
FIG. 9 is a graph plotting growth (OD) verses time (hours) for K. marxianus cultured with a corn fiber hydrolysate at 30° C.

The yeast cells were capable of generating biomass when cultured with corn fiber hydrolysate (FIG. 9).

4. Various pH Conditions

Figure 10:
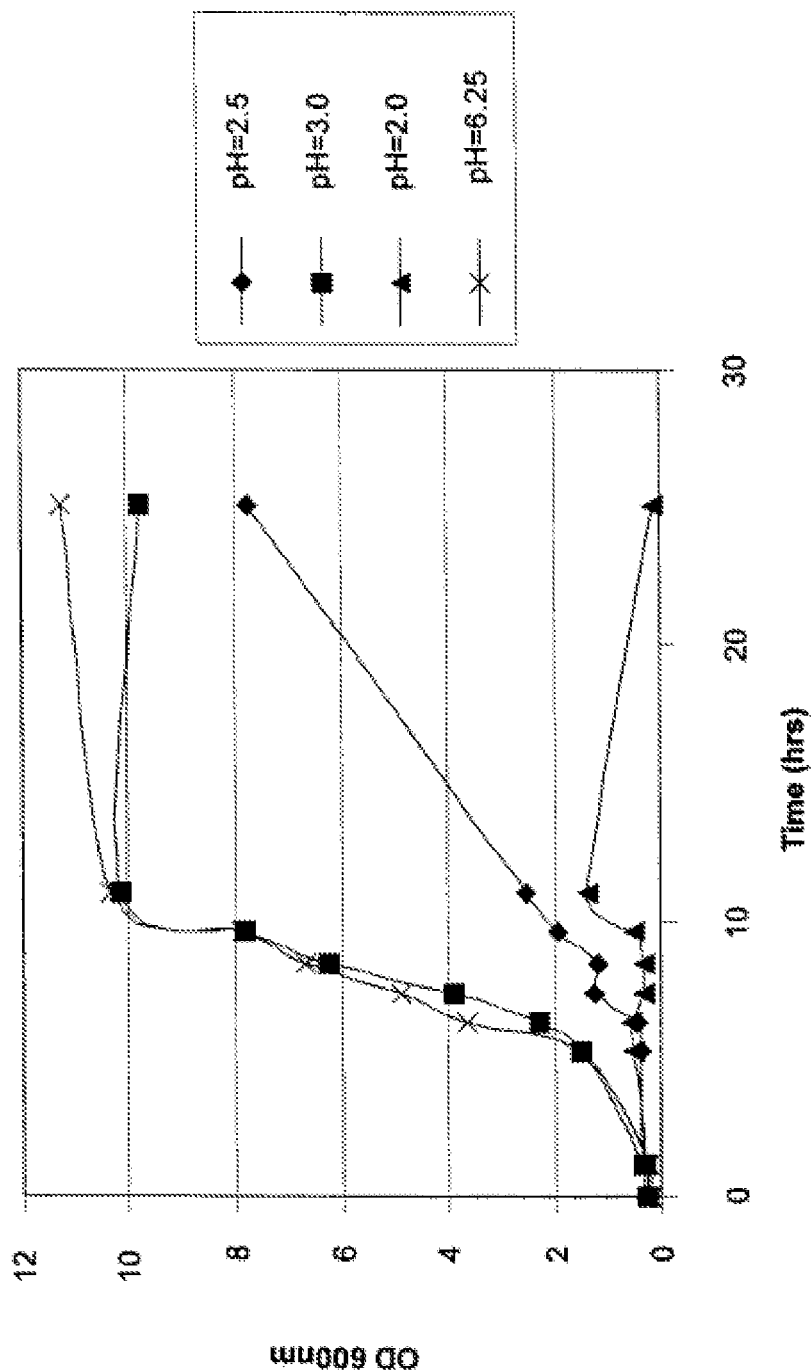
FIG. 10 is a graph plotting growth (OD) verses time (hours) for K. marxianus cultured at 30° C. and the indicated pH.

Overnight cultures of *K. marxianus* were inoculated into four flasks containing 50 mL yeast YPD medium (yeast extract 10 g/L, peptone broth 20 g/L, glucose 20 g/L). Each flask had a different pH, which was adjusted using HCl. During the culturing experiment, the temperature was maintained at 30° C., and OD measurements were made periodically. Growth was observed within each flask (FIG. 10).

5. Various pH Conditions/Lactic Acid

Figure 11:
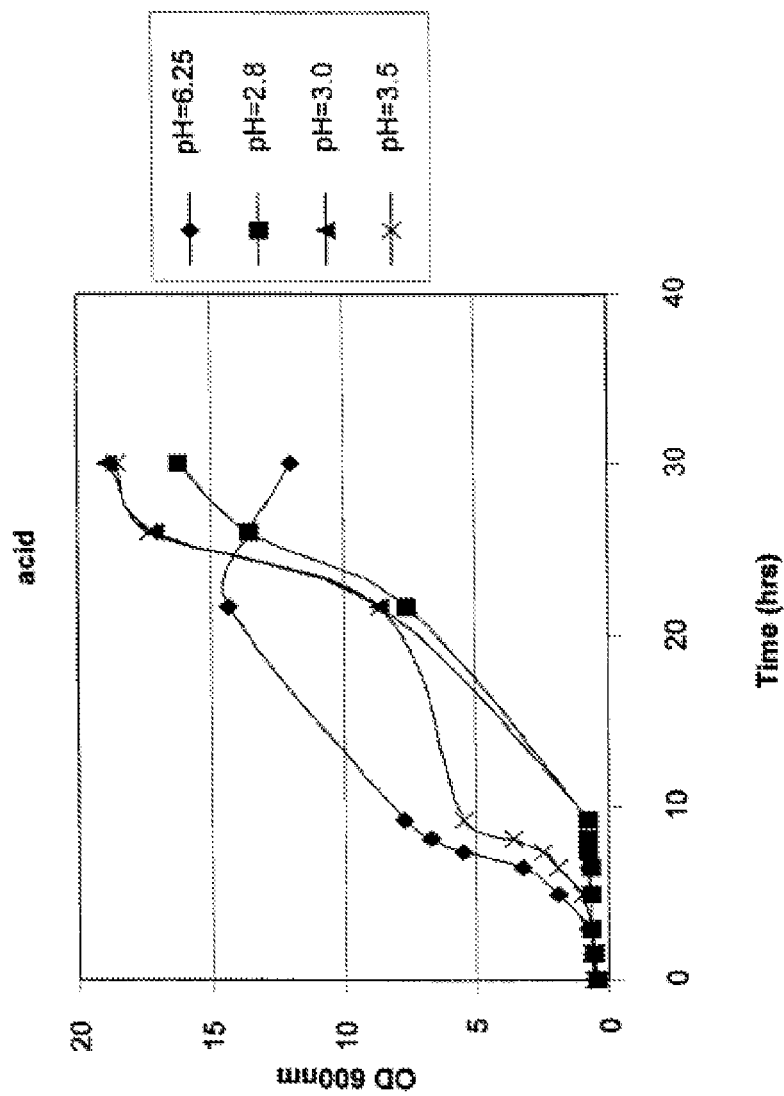
FIG. 11 is a graph plotting growth (OD) verses time (hours) for K. marxianus cultured at 30° C. and the indicated pH in the presence of 40 grams of lactic acid.
Figure 12:
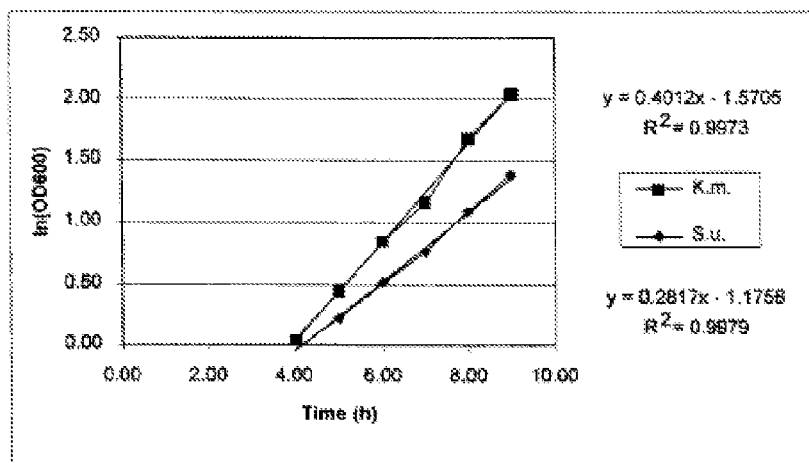
FIG. 12 shows three graphs plotting (A) biomass production; (B) glucose consumption; and (C) ethanol production of S. uvarum and K. marxianus when cultured on mineral medium with 2% glucose under aerobic conditions.
Figure 12:
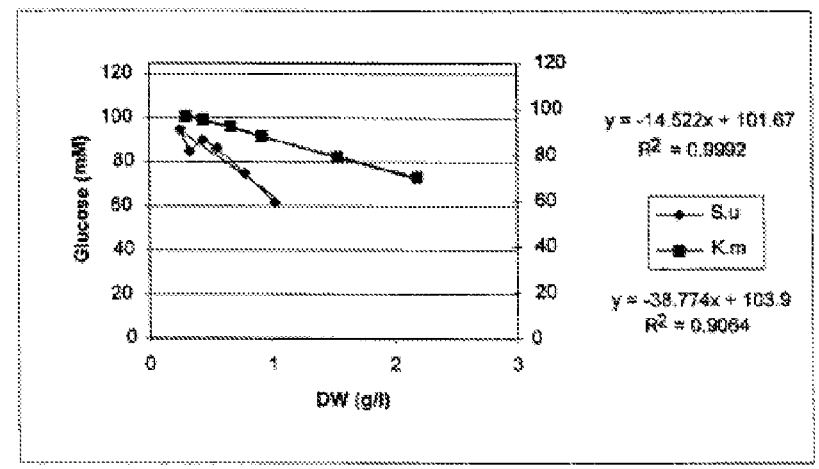
Figure 12:
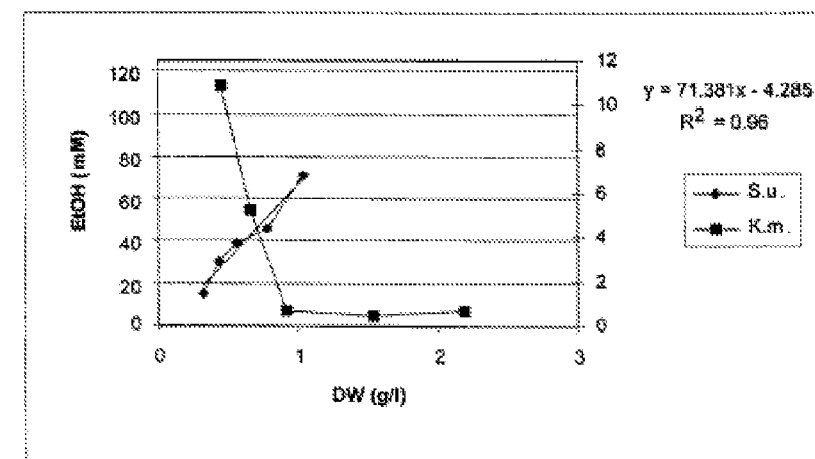
Figure 13:
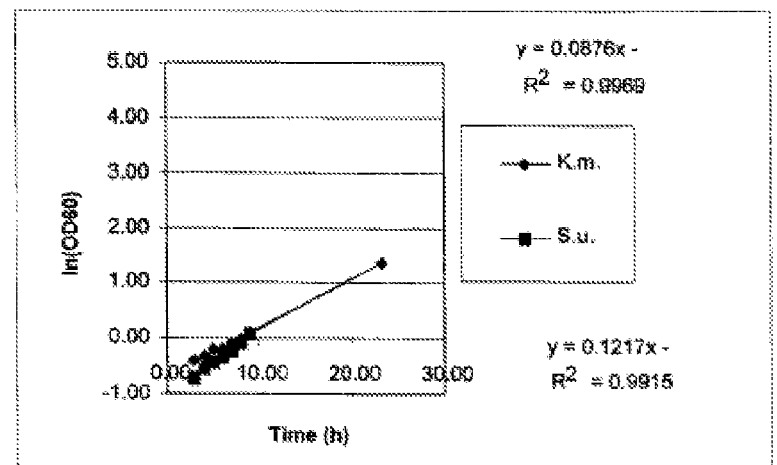
FIG. 13 shows three graphs plotting (A) biomass production; (B) glucose consumption; and (C) ethanol production of S. uvarum and K. marxianus when cultured on mineral medium with 2% glucose under anaerobic conditions.
Figure 13:
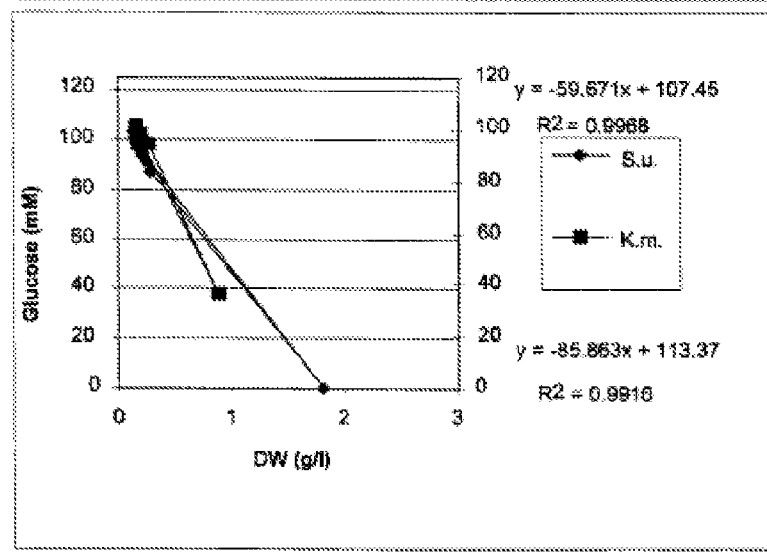
Figure 13:
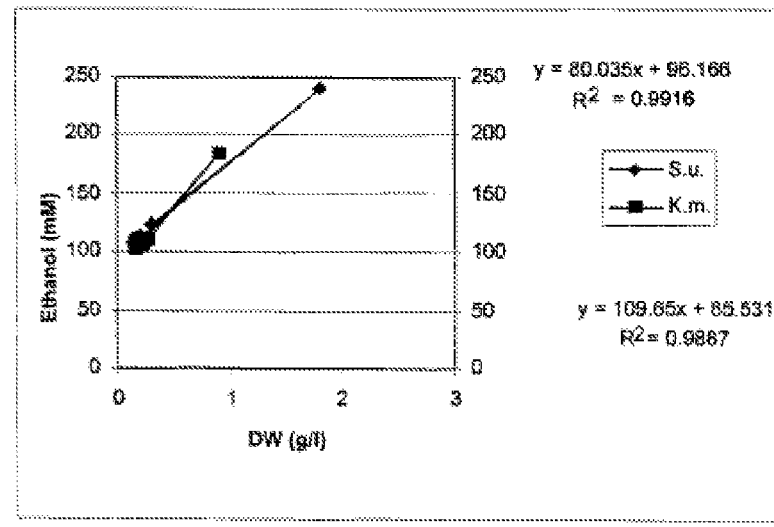

Overnight cultures of *K. marxianus* were inoculated into four flasks containing 50 mL yeast YPD medium (yeast extract 10 g/L, peptone broth 20 g/L, glucose 20 g/L) as well as 40 g/L lactic acid. The addition of the lactic acid resulted in a pH of 2.8. Thus, the pH within three flasks was adjusted to the indicated pH using NaOH. During the culturing experiment, the temperature was maintained at 30° C., and OD measurements were made periodically. Growth was observed within each flask (FIG. 11).

Example 9

Recombinant Cells Capable of Producing Acrylyl-CoA

An organism incapable of utilizing acrylate as a carbon source (e.g., *E. coli*) is transformed with a *Clostridium propionicum* genomic DNA library. The *C. propionicum* genomic library is generated using the pHES plasmid such that it expresses 10 kbp fragments of the *C. propionicum* genome. The transformed *E. coli* are plated on selection media with only acrylic acid as a carbon source. Only those cells that have the ability to assimilate acrylate will grow. Acrylate is normally assimilated by its enzyme-mediated conversion into lactate. In turn, lactate can be converted into pyruvate and utilized by the cells via the Krebs cycle.

Once a transformed *E. coli* is selected, the DNA plasmid from the genomic library is isolated, and the inserted fragment sequenced. Once sequenced, the fragment is scanned for open reading frames to determine the coding sequence for enzymes involved in the conversion between lactate and acrylate (e.g., lactoyl-CoA dehydrogenase and CoA transferases).

The isolated clones containing the coding sequence for these enzymes is introduced into the yeast cells described in Example 6, which contain lactate dehydrogenase and lack pyruvate decarboxylase activity. Selection of recombinant yeast cells that contain the introduced nucleic acid is performed using G418 (300 g/L). Once isolated, the recombinant yeast cells are grown aerobically on glucose, and then switched to anaerobic conditions. The broth then is collected and assayed to acrylate using standard HPLC methods as described by Danner et at. (Biotechnological production of acrylic acid from biomass, In: *Applied Biochemistry and Biotechnology*, Vol. 70-72 (1998)).

Example 10

Recombinant Cells Capable of Producing Ascorbate

Expression vectors are engineered such that the following polypeptides are expressed: 2,5-dioxovalerate dehydrogenase, 5-dehydro-4-deoxy-D-glucarate dehydratase, glucarate dehydratase, aldehyde dehydratase, glucuronolactone reductase, and L-gluconolactone oxidase. The nucleic acid sequence encoding these polypeptides are isolated from various microorganisms. Once engineered, the expression vectors are transformed into a yeast cells by electroporation. Once transformed, the yeast cells are analyzed to determine whether or not they produce L-ascorbate.

Example 11

Recombinant Cells Capable of Producing D-Xylose

Expression vectors are engineered such that the following polypeptides are expressed: 2-dehydro-3-deoxy-D-pentanoate aldolase, xylonate dehydratase, xylonotactonase, and D-xylose dehydrogenase. The nucleic acid sequences encoding these polypeptides are isolated from *Pseudomonas* sp. Once engineered, the expression vectors are transformed into yeast cells by electroporation. Once transformed, the yeast cells are analyzed to determine whether or not they produce D-xylose or other pentose carbon compounds.

Example 12

Recombinant Cells Capable of Producing Citrate

PCR primers are designed based on the *S. cerevisiae* aconitase (ACO1, Genbank accession number M33131) nucleic acid sequence. These primers are used to clone the aconitase encoding nucleic acid from a *Kluyveromyces, Yamadazyma*, or *Honsenula* species. Once sequenced, linear constructs are made as described in Example 5, and used to disrupt the aconitase encoding nucleic acid within yeast cells. The selection marker used is the antibiotic G418 instead of lactate production as described in Example 5. The nucleic acid providing resistance to antibiotic G418 is the neomycin/kanamycin gene. This gene is obtained from the pPIC9K vector (InVitrogen), and inserted into the pHES vector. Yeast cells are transformed with PCR generated linear fragments that are engineered to have ends homologous to the ACO1 as described above. The linear fragment is designed to encode the G418 resistance gene. Only cells that have integrated the linear fragment in the location of the aconitase encoding nucleic acid are resistant to the antibiotic. Those cells are analyzed for the appropriate integration using PCR. The yeast cells obtained by this method have a partially functional TCA cycle, and thus can overproduce citrate. The citrate is transported across the mitochondrial membrane and into the broth. In addition, these yeast cells are given an exogenous nucleic acid molecule that encodes an enzyme such as ATP-citrate lyase such that they can catalyze the conversion of accumulated citrate into oxaloacetate (see Example 13).

Example 13

Recombinant Cells Capable of Expressing Citrate Lyase in the Cytosol

A crabtree positive yeast cell is transformed with the pHES plasmid containing a nucleic acid sequence that encodes a polypeptide having ATP-citrate lyase activity. This nucleic acid is isolated from *E. coli*, *Krebsiella pneumoniae* (Genbank accession number X79817), or other published sources. Once transformed, the yeast cells are analyzed to determine whether or not they can utilize sugars to produce large amounts of lipid accumulation. In addition, the yeast cells are analyzed to determine whether or not they exhibit ATP-citrate lyase activity as described by Holdsworth et al. (*J. Gen. Microbiol.*, 134:2907-2915 (1998)). The yeast cells having ATP-citrate lyase activity are capable of providing cytosolic acetate under aerobic conditions by a route other than the breakdown of aldehyde to acetate via aldehyde dehydrogenase. In addition, when such yeast lack pyruvate decarboxylase or aldehyde dehydrogenase activity, they should be able to provide acetate for biosynthesis via the Krebs cycle.

Example 14

Recombinant Cells Unable to Utilize Lactate as Carbon Source

Yeast cells are engineered such that the activity of a carboxylic acid transporter similar to the *S. cerevisiae* JEN1 polypeptide is reduced, Such yeast cells will have a reduced ability to transport lactate, and hence utilize lactate less efficiently. The activity of the carboxylic acid transporter within yeast cells is reduced by disrupting the locus containing the coding sequence for this polypeptide. First, the homologue of the JEN1 polypeptide is isolated from a host cell using degenerate primers designed based on the available sequence for JEN1 (Genbank accession number U24155). Once the nucleic acid is isolated from the host cell, it is sequenced. Disruption of the coding sequence for this polypeptide is done using the procedures described in Example 11. Linear fragments are generated encoding homologous regions to the JEN1 sequence as well as the entire G418 resistance gene. This linear fragment is integrated into the JEN1 genomic sequence causing disruption of the activity. Cells lacking carboxylic acid transporter activity are identified by their inability to transport carboxylic acid, and hence their inability to grow when cultured on lactate.

In addition, cells are modified such that the activity of a functional equivalent of the *S. cerevisiae* cytochrome b2 polypeptide is reduced. The cytochrome b2 polypeptide enables *S. cerevisiae* cells to metabolize lactate within the mitochondria. First, degenerate primers are designed from the *Saccharomyces* cytochrome b2 sequence (Genbank accession number Z46729). Once isolated, the clone is sequenced. The disruption of the yeast host homologue of cytochrome b2 is done using methods described in Methods in Yeast Genetics (Eds. Alison et al., Cold Spring Harbor Press (1997)). This recombinant yeast cell will be unable to utilize lactate as a carbon source.

Example 15

Large-Scale Production of Lactate

Multiple variants of *K. marxianus* cells having reduced PDC activity are produced and isolated. Each variant is engineered to contain a different copy number of an exogenous nucleic acid molecule encoding a polypeptide having LDH activity. The LDH polypeptide is from multiple different sources. Such variant cells can have different specific productivity for lactic acid at 40° C.

Each variant is grown in a vessel under aerobic conditions with an air flow of 1.5 VVM and a dissolved oxygen content of 30% to reach a cell density of about 60 g/L, dry basis. Once the density is sufficient, the air flow is turned off, and the conditions within the vessel are switched to anaerobic conditions. No base is added. The variants with the highest specific productivity during the anaerobic phase can be found not only to produce lactic acid faster, but also to achieve a higher concentration at a lower pH, than the variants with lower specific productivity. Product yield on glucose during the production phase can exceed 90%.

Certain variants are selected and subjected to the same culturing methods except that the air flow is reduced to 0.1 VVM, rather than being completely shut off. Under such conditions, the final pH within the vessel can be lower, and the lactate concentration can be higher than the conditions with no air flow. Product yield on glucose can be reduced but can remain at about 90%. When the test is repeated, but with an air flow of 0.5 VVM, the product yield on glucose can be reduced to less than 80%.

Example 16

Large-Scale Production of Lactate Using a Series of Batch Fermentations

A culture of *K. marxianus* lacking PDC activity and having LDH activity is used as the inoculum in a series of batch fermentations. Each fermentation is carried out in progressively larger vessels, each of which is sterilized immediately prior to use. In addition, each vessel is provided with an air flow of 1.5 VVM and stirring sufficient to maintain a dissolved oxygen content above 10%. The final vessel has a volume of 6,000 L. The vessels also are maintained at a temperature of 45° C. to enhance survival of the genetically modified *K. marxianus* cells over wild-type yeast and other microorganisms. Each vessel is filled with standard culture medium for optimal growth.

The contents of the final vessel, with a cell density of 100 grams of cells/L, dry basis, are transferred to a recently steamed production vessel having a volume of 300,000 L.

Optionally, additional cells obtained from the filtration of a previous production process are added. The cell density in the production vessel is 6 grams of cells/L, dry basis. Glucose is added to a level of 80 g/L. The conditions within the vessel are anaerobic with the temperature being 42° C. for a period of 25 hours. The specific productivity is greater than 0.5 grams lactate/(gram biomass*hour) until near the end of the process, at which time the productivity begins to drop. Once productivity begins to drop, the cells are removed and saved for reuse. The final lactate concentration can be 75 g/L with the pH being 2.8. After biomass removal, the solution is concentrated by evaporation to a concentration of 50% lactate. The free acid (about 86% of total lactate) is extracted by liquid extraction into an organic and back extracted at a higher temperature into water. The raffinate containing the lactate salt is either cleaned and recycled as a buffer in the growth vessel, or acidified with, for example, sulfuric acid and purified.

Example 17

Comparison of Aerobic Production of a Crabtree Negative (*K. marxianus*) and a Crabtree Positive (*S. uvarum*) Organisms A crabtree negative (*K. marxianus*) and a crabtree positive (*S. ovarum*) organism were each grown in aerobic and anaerobic batch fermenters. Batch cultivation was performed at 30° C. in laboratory fermenters with a working volume of 1.5 L. The pH was maintained at 5.0±0.1 bp automated addition of 2 mol·L$^{-1}$ potassium hydroxide (KOH). The fermentor was flushed with air (aerobic cultures) or nitrogen gas (anaerobic cultures) at a flow rate of 0.8 1-min$^{-1}$ and stirred at 800 rpm. The dissolved-oxygen concentration was continuously monitored with an oxygen electrode (Ingold, type 34 100 3002). In the aerobic cultures, the dissolved oxygen concentration was maintained above 60%. 10 ml samples were withdrawn at appropriate intervals for determination of dry weight and metabolite concentrations. Tween-80 and ergosterot were added to anaerobic cultures to supply the compounds required for fatty acid synthesis.

During exponential growth, both the dry weight and OD660 of yeast cultures, and the glucose and ethanol concentration in the supernatant were determined at appropriate intervals. The specific ethanol production rate ($q_{ethanol}$, mmol·g$^{-1}$·h$^{-1}$) was calculated by the following equation using linear regression analysis:

$$q_{ethanol} = \frac{dE}{dC_x} \cdot \mu_{max}$$

dE/dt (the rate of increase of the ethanol concentration in the culture; mmol·L$^{-1}$·h$^{-1}$) and dC$_x$/dt (the rate of increase of the biomass concentration; g·L$^{-1}$·h$^{-1}$) were calculated using differentiation of plots of ethanol concentration and biomass concentration versus time. $\mu_{max}$ (h$^{-1}$). The maximum specific growth rate on glucose was estimated from the exponential part of a plot of $C_x$ versus time. To calculate the specific glucose consumption rate ($q_{glucose}$, mmol·g$^{-1}$·h$^{-1}$), dE was replaced by dG (amount of glucose consumed per hour).

In the aerobic hatch cultures, the *Kluyveromyces* and the *Saccharomyces* strains exhibited a maximum specific growth rate on glucose of 0.4 h$^{-1}$ and 0.28 h$^{-1}$, respectively. The high glucose concentration and the resulting high specific growth rate of the *Saccharomyces* culture resulted in high rates of aerobic alcoholic fermentation (Table 3, FIG. 1). The specific rate of glucose consumption was about 2-fold higher in the *Saccharomyces* strain compared to the *Kluyveromyces* strain due to the vigorous alcoholic fermentation. From an energetic standpoint, alcoholic fermentation is a less efficient way for the cell to generate ATP. The biomass yield on glucose was 0.38 g/g for *Kluyveromyces* and 0.14 g/g for the *Saccharomyces uvarum*. The ethanol yield on glucose was zero for the crabtree-negative phenotype *Kluyveromyces* strain and 1.83 mmol/mmol for the *Saccharomyces*, the crabtree-positive phenotype, culture.

TABLE 3

Maximum specific growth rate, specific rates (q, mmol[g biomass]$^{-1}$ h$^{-1}$) of ethanol production and glucose consumption, the biomass yield (g/g), product yield (mmol/mmol), and carbon recovery (in %; only calculated for anaerobic cultures) during exponential growth in batch cultures of *Saccharomyces uvarum* and *Kluyveromyces marxianus* on mineral medium containing 2% (wt/vol) glucose.

| | K. marxianus | | S. uvarum | |
|---|---|---|---|---|
| | aerobic | anaerobic | aerobic | anaerobic |
| $\mu_{max}$ (h$^{-1}$) | 0.38 | 0.09 | 0.28 | 0.12 |
| $q_{glucose}$ | 5.8 | 7.6 | 10.9 | 7.2 |
| $q_{ethanol}$ | 0 | 9.9 | 20 | 9.7 |
| $Y_{p/s}$ | 0 | 1.30 | 1.83 | 1.35 |
| $Y_{x/s}$ | 0.38 | 0.07 | 0.14 | 0.09 |
| C-rec | — | 84.6 | — | 73.3 |

In anaerobic batch cultures, the specific growth rate and biomass yield for both strains was very low compared to that found under aerobic conditions (Table 3, FIGS. 1 and 2). For the *Kluyveromyces* and the *Saccharomyces* strains, the biomass yield was 0.07 and 0.09 g/g, respectively. Both the strains perform equally well with respect to the specific rate of alcoholic fermentation under anaerobic conditions. This was confirmed using CO$_2$ production data.

Generally, this Example demonstrates that aerobic production of biomass is much faster than anaerobic, and that yield of biomass under aerobic conditions is higher for crabtree negative organisms (because, in crabtree positive organisms, some alcoholic fermentation takes place, using up glucose). This Example also demonstrates that the fermentation product (ethanol, in this case) is produced at the same rate for both crabtree positive and negative organisms under anaerobic conditions. Thus, an aerobic growth stage provides the high biomass yield, and a subsequent anaerobic fermentation stage channels metabolic energy into product formation (rather than more growth). Overall, a process in which production is separated from growth provides greater process flexibility and better control over the overall process yield.

Example 18

Improved Lactate Production in a Host Strain that Naturally Makes L-Lactic Acid: Amplification of Linear Fragments of Homologous DNA for Gene Disruptions of Pyruvate Decarboxylase The yeast *Kluyveromyces thermotolerans* (*K. thermotolerans*) is a natural producer of L-lactic acid (Kurtzman and Fell, (1998) "*The Yeasts, A Taxonomic Study*" pp. 240-241; Elsevier Science B. V.; Amsterdam, The Netherlands). *K. thermotolerans* has a naturally occurring lactate dehydrogenase (ldh) gene that allows for the production of L-lactic acid. The amount of lactic acid produced under anaerobic conditions is approximately 4% g/g of glucose utilized, while the remainder of the glucose is essentially converted into ethanol (42.5% g/g glucose consumed), glycerol (3% g/g of glucose consumed) and acetate (0.3 g/g % of glucose consumed).

TABLE 4

Results of anaerobic fermentation using *K. thermotolerans*, starting with 100 g/l glucose in YPAD media (rich media).

| Time | glucose | lactic | acetate | glycerol | ethanol | Lactic YSI |
|------|---------|--------|---------|----------|---------|------------|
| 0    | 92.937  | 0      | 0       | 0        | 0.025   | 0.06       |
| 12   | 79.603  | 0.476  | 0       | 0.41     | 3.345   | 0.6        |
| 36   | 38.618  | 2.135  | 0       | 2.011    | 25.642  | 2.08       |
| 54   | 11.662  | 3.525  | 0.2     | 2.789    | 41.522  | 3.34       |
| 78   | 1.539   | 4.322  | 0.209   | 3.213    | 42.5    | 3.88       |
| 98   | 0.286   | 4.365  | 0.307   | 3.24     | 42.5    | 3.74       |

A 600 bp region of the PDC1 was isolated from *K. thermotolerans* using consensus primers constructed from a sequence derived by comparing the PDC1 gene sequence from *K. marxianus* and *K. lactis*. The PDC1 fragment was then sequenced (Sanger), and used to isolate a 7.5 kbp fragment surrounding the *K. thermotolerans* pdcl (FIG. 6e) using PCR and genome walking techniques (Clonetech). The 7.5 kbp fragment was then cloned into the pCRII TA cloning vector (Invitrogen). A portion of approximately 730 bp near the middle of the coding region of PDC1 was removed from the *K. thermotolerans* 7.5 kbp fragment. The portion of *K. thermotolerans* pdcl removed by restriction digests (Sambrook) contained the sequence identified as SEQ ID NO. 11. A gene encoding kanamycin resistance, including its promoter, was then isolated from pPIC9K vector (Invitrogen) by restriction digestion (Sambrook), and cloned into the site in the 7.5 kbp that from which the 730 bp fragment was removed. The sequence of the kanamycin resistance gene and its promoter from pPIC9K (Invitrogen) is identified as SEQ ID NO: 9. The resulting construct includes the kanamycin resistance gene (G418) surrounded by approximately 6.8 kbp of the PDC region as shown in FIG. 6f.

Figure 6F:
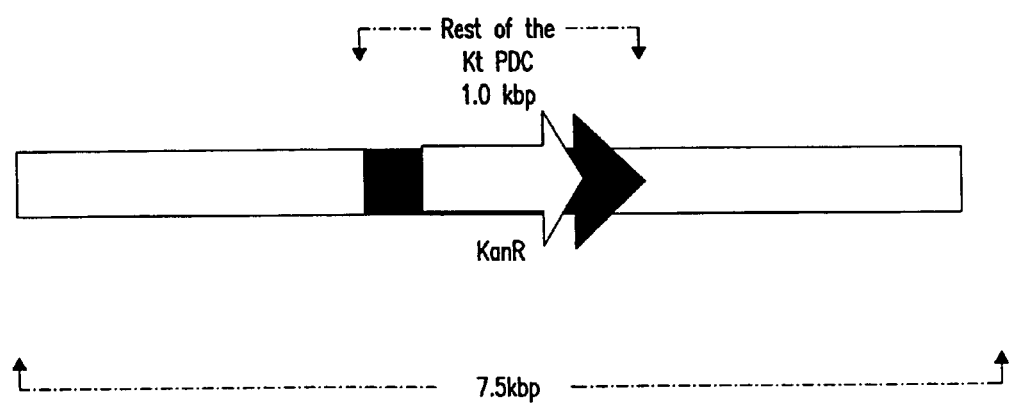
FIG. 6f is a diagram depicting the deletion of 750 bp from the 1.7 kbp PDC1 gene and the insertion of the kanamycin resistance gene.

The construct depicted in FIG. 6f is digested with two restriction enzymes (Sambrook) to yield approximately 3 micrograms of fragment DNA containing the homologous PDC region and the mid-sequence inserted kanamyacin resistance gene. *K. thermotolerans* is transformed with the fragment using known transformation techniques, such as electroporation to disrupt the PDC of *K. thermotolerans*. The method of electroporation is as follows: a) grow culture in YPAD overnight (~15 hr) in a volume of 20 ml; b) transfer 500 ul of culture to a microfuge tube, spin @4K, 4 min, discard supernatant; c) wash with 1 ml cold EB. (EB=Electroporation Buffer: 10 mM Tris-HCl, pH 7.5; 270 mM Sucrose; 1 mM $MgCl_2$); d) resuspended in 1 ml IB (IB=Incubation Buffer: YPD; 25 mM DTT; 20 mM Hepes, pH8.0.); e) shake @ 800 rpm, 30° C. for 30 min in an Eppendorf Thermomixer; f) spin down, wash once with EB, resuspend in 400 ul EB; g) add three micrograms fragment DNA (in water 10 mM Tris-Ct, pH 8.5), incubate on ice 30 min; h) transfer to 0.4 cm electroporation cuvette. Bio-Rad Gene Pulser settings: 1000V, 1000Ω, 50 μF. Time constant after pulse: ~20 msec; i) transfer to 3 ml Morton Closure tube, incubate without shaking at 30° C. for 1 hour; j) add 400 ul liquid YPAD media (YPAD: 10 g Yeast Extract; 20 g Peptone; 20 g Glucose; 100 mg Adenine Hemisulphate. Volume 1 L. No pH adjustment), shake 800 rpm, 30° C. for 1 hour in Eppendorf Thermomixer; k) add 400 ul liquid yPAD and recover 4-6 hours; l) spin down in microfuge tube @ 4K, 4 min, discard supernatant, resuspend in 400 ul lM Sorbitol and plate onto 100 ug/ml G418 selective plates; and m) incubate at 30° C. for three to five days.

Colonies are screened first by a second patching onto a culture dish containing 200 ug/ml G418. The genomic DNA is isolated from the secondary yeast patch using standard genomic preparations (Sambrook). The isolated genomic is then screened via PCR for 1) the presence of the kanamycin fragment using suitable primers and conditions (Sambrook); and 2) the absence of the disrupted PDC region using suitable primers and PCR conditions. Colonies positive for the selection marker and negative for the PDC disruption region are then grown for further study, for example, genomic DNA from these strains is further analyzed by southern hybridization analysis.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for making lactic acid, said method comprising:
   a) providing a microorganism exhibiting a crabtree-negative phenotype and transformed with at least one exogenous gene encoding lactate dehydrogenase;
   b) culturing the crabtree-negative microorganism in a first culture medium which includes a carbon source under a first set of culture conditions which promote cellular respiration; and
   c) culturing the crabtree-negative microorganism in a second culture medium which includes a carbon source under a second set of culture conditions which promote production of lactic acid.

2. A method for making lactic acid, comprising
   a) providing a microorganism exhibiting a crabtree-negative phenotype selected from the group consisting of *Kluyveromyces, Pichia, Candida* and *Hansenula* and transformed with at least one exogenous gene encoding lactate dehydrogenase;
   b) culturing said crabtree-negative microorganism in a first culture medium which includes a carbon source comprising glucose and under a first set of culture conditions, including a dissolved oxygen content of at least 20 percent relative to the amount present at saturated conditions with air at atmospheric pressure, which promote cellular respiration; and
   c) then culturing the crabtree-negative microorganism in a culture medium which includes a carbon source comprising glucose under a second set of culture conditions, including a dissolved oxygen content of less than 2.0 percent relative to the amount present at saturated conditions with air at atmospheric pressure, which promote the production of lactic acid.

3. A method for making lactic acid, comprising
   a) providing a microorganism exhibiting a crabtree-negative phenotype selected from the group consisting of *Kluyveromyces, Pichia, Candida* and *Hansenula* and transformed with at least one exogenous gene encoding lactate dehydrogenase;
   b) culturing said crabtree-negative microorganism in a first culture medium which includes a carbon source comprising glucose and under a first set of culture conditions which promote cellular respiration; and c) then culturing the crabtree-negative microorganism in a culture medium which includes a carbon source comprising glucose under a second set of culture conditions, including an acidic pH of greater than 1.5, which promote the production of lactic acid.

4. A method for making lactic acid, comprising a) providing a microorganism exhibiting a crabtree-negative phenotype selected from the group consisting of *Kluyveromyces, Pichia, Candida* and *Hansenula* and transformed with at least one exogenous gene encoding lactate dehydrogenase and having a reduced pyruvate decarboxylase activity;

b) culturing said crabtree-negative microorganism in a first culture medium which includes a carbon source comprising glucose and under a first set of culture conditions which promote cellular respiration; and c) then culturing the crabtree-negative microorganism in a culture medium which includes a carbon source comprising glucose under a second set of culture conditions which promote the production of lactic acid.

* * * * *

SEQUENCE LISTING

<160> NUMBER OF SEQ ID NOS: 11

<210> SEQ ID NO 1
<211> LENGTH: 92
<212> TYPE: DNA
<213> ORGANISM: Artificial
<220> FEATURE:
<223> OTHER INFORMATION: Synthetic

<400> SEQUENCE: 1
cccaagcttg aattccccgg gggatccctg cagggtacca cgcgtagatc tactagtgcg    60
gccgcctcga gtctagaggg cccaagcttg gg    92

<210> SEQ ID NO 2
<211> LENGTH: 91
<212> TYPE: DNA
<213> ORGANISM: Artificial

-continued

```
<220> FEATURE:
<223> OTHER INFORMATION: Synthetic

<400> SEQUENCE: 2
ccaagcttgg gccctctaga ctcgaggcgg ccgcactagt agatctacgc gtggtaccct      60
gcagggatcc cccggggaat tcaagcttgg g                                    91

<210> SEQ ID NO 3
<211> LENGTH: 31
<212> TYPE: DNA
<213> ORGANISM: Artificial
<220> FEATURE:
<223> OTHER INFORMATION: Synthetic

<400> SEQUENCE: 3
ccgggatcca tggcaagaga ggaaaaacct c                                    31

<210> SEQ ID NO 4
<211> LENGTH: 32
<212> TYPE: DNA
<213> ORGANISM: Artificial
<220> FEATURE:
<223> OTHER INFORMATION: Synthetic

<400> SEQUENCE: 4
ccaagatctt tattgacgaa ccttaacgcc ag                                   32

<210> SEQ ID NO 5
<211> LENGTH: 37
<212> TYPE: DNA
<213> ORGANISM: Artificial
<220> FEATURE:
<223> OTHER INFORMATION: Synthetic

<400> SEQUENCE: 5
ccgggatcca tgtctaatat tcaaaatcat caaaaag                              37

<210> SEQ ID NO 6
<211> LENGTH: 33
<212> TYPE: DNA
<213> ORGANISM: Artificial
<220> FEATURE:
<223> OTHER INFORMATION: Synthetic

<400> SEQUENCE: 6
ccaagatctt tatttgtctt gttttttcagc aag                                 33

<210> SEQ ID NO 7
<211> LENGTH: 82
<212> TYPE: DNA
<213> ORGANISM: Artificial
<220> FEATURE:
<223> OTHER INFORMATION: Synthetic

<400> SEQUENCE: 7
taaacagtac aatcgcaaag aaaagctcca cacccaaacc aaataattgc aatgcaactt     60
cttttctttt tttttctttt ct                                              82

<210> SEQ ID NO 8
<211> LENGTH: 79
<212> TYPE: DNA
<213> ORGANISM: Artificial
<220> FEATURE:
<223> OTHER INFORMATION: Synthetic
```

-continued

<400> SEQUENCE: 8

```
ttataaaatc attaaaatcc aaaatcgtaa tttatctctt tatcctctcc ctctctacat    60
gccggtagag gtgtggtca                                                 79
```

<210> SEQ ID NO 9
<211> LENGTH: 1738
<212> TYPE: DNA
<213> ORGANISM: Artificial
<220> FEATURE:
<223> OTHER INFORMATION: Synthetic

<400> SEQUENCE: 9

```
gtacaacttg agcaagttgt cgatcagctc ctcaaattgg tcctctgtaa cggatgactc    60
aacttgcaca ttaacttgaa gctcagtcga ttgagtgaac ttgatcaggt tgtgcagctg   120
gtcagcagca tagggaaaca cggcttttcc taccaaactc aaggaattat caaactctgc   180
aacacttgcg tatgcaggta gcaagggaaa tgtcatactt gaagtcggac agtgagtgta   240
gtcttgagaa attctgaagc cgtatttta ttatcagtga gtcagtcatc aggagatcct    300
ctacgccgga cgcatcgtgg ccgacctgca ggggggggg gggcgctgag gtctgcctcg    360
tgaagaaggt gttgctgact cataccaggc ctgaatcgcc ccatcatcca gccagaaagt   420
gagggagcca cggttgatga gagctttgtt gtaggtggac cagttggtga ttttgaactt   480
ttgctttgcc acggaacggt ctgcgttgtc gggaagatgc gtgatctgat ccttcaactc   540
agcaaaagtt cgatttattc aacaaagccg ccgtcccgtc aagtcagcgt aatgctctgc   600
cagtgttaca accaattaac caattctgat tagaaaaact catcgagcat caaatgaaac   660
tgcaatttat tcatatcagg attatcaata ccatattttt gaaaaagccg tttctgtaat   720
gaaggagaaa actcaccgag gcagttccat aggatggcaa gatcctggta tcggtctgcg   780
attccgactc gtccaacatc aatacaacct attaatttcc cctcgtcaaa ataaggtta    840 tcaagtgaga atcaccatg agtgacgact gaatccggtg agaatggcaa aagcttatgc   900 atttcttcc agacttgttc aacaggccag ccattacgct cgtcatcaaa atcactcgca   960
tcaaccaaac cgttattcat tcgtgattgc gcctgagcga gacgaaatac gcgatcgctg  1020
ttaaaaggac aattacaaac aggaatcgaa tgcaaccggc gcaggaacac tgccagcgca  1080
tcaacaatat tttcacctga atcaggatat tcttctaata cctggaatgc tgttttcccg  1140
gggatcgcag tggtgagtaa ccatgcatca tcaggagtac ggataaaatg cttgatggtc  1200
ggaagaggca taaattccgt cagccagttt agtctgacca tctcatctgt aacatcattg  1260
gcaacgctac ctttgccatg tttcagaaac aactctggcg catcgggctt cccatacaat  1320
cgatagattg tcgcacctga ttgcccgaca ttatcgcgag cccatttata cccatataaa  1380
tcagcatcca tgttggaatt taatcgcggc ctcgagcaag acgtttcccg ttgaatatgg  1440
ctcataacac cccttgtatt actgtttatg taagcagaca gttttattgt tcatgatgat  1500
atatttttat cttgtgcaat gtaacatcag agattttgag acacaacgtg ctttcccccc  1560
ccccccctgc aggtcggcat caccggcgcc acaggtgcgg ttgctggcgc ctatatcgcc  1620
gacatcaccg atggggaaga tcgggctcgc cacttcgggc tcatgagcgc ttgtttcggc  1680
gtgggtatgg tggcaggccc cgtggccggg ggactgttgg gcgccatctc cttgcatg   1738
```

<210> SEQ ID NO 10
<211> LENGTH: 372
<212> TYPE: DNA
<213> ORGANISM: Kluyveromyces marxianus

```
<400> SEQUENCE: 10
ccggttcttt ctcttactct tacaagacca agaacattgt cgaattccac tccgactaca      60
tcaaggtcag aaacgccact ttcccaggtg tccaaatgaa gttcgtcttg caaaagttgt     120
tgaccaaggt caaggatgct gctaagggtt acaagccagt tccagttcct cacgctccaa    180
gagacaacaa gccagttgct gactctactc cattgaagca agaatgggtc tggactcaag    240
tcggtaagtt cctacaagaa ggtgatgttg ttctaactga aaccggtacc tccgctttcg    300
gtatcaacca aacccacttc ccaaatgaca cctacggtat ctcccaagtc ttgtggggtt    360
ccattggttt ca                                                         372

<210> SEQ ID NO 11
<211> LENGTH: 747
<212> TYPE: DNA
<213> ORGANISM: Kluyveromyces thermotolerans

<400> SEQUENCE: 11
ttaccactgt cttcggtctg ccaggtgact tcaatctgcg tctgttggac gagatctacg      60
aggtcgaggg tatgagatgg gccggtaact gtaacgagtt gaacgcttct tacgctgccg    120
acgcttacgc cagaatcaag ggtatgtcct gtttgatcac caccttcggt gtcggtgagt    180
tgtccgcttt gaacggtatc gccggttctt acgctgagca cgtcggtgtc ttgcacattg    240
tcggtgtccc atccgtctcc gcccaggcca agcagctatt gttgcaccac accttgggta    300
acggtgactt cactgtcttc cacagaatgt ccgccaacat ctctgagacc actgctatga    360
tcactgatct agctaccgcc ccatctgaga tcgacagatg tatcagaacc acctacatta    420
gacagagacc tgtctacttg ggtttgccat ctaacttcgt tgaccagatg gtcccagcct    480
ctctattgga caccccaatt gacttggcct tgaagccaaa cgaccagcag gctgaggagg    540
aggtcatctc tactttgttg gagatgatca aggacgctaa gaacccagtc atcttggctg    600
acgcttgcgc ttccagacac gatgtcaagg ctgagaccaa gaagttgatt gacatcactc    660
agttcccatc tttcgttacc ccaatgggta agggttccat tgacgagaag cacccaagat    720
tcggtggtgt ctacgtcggt accttgt                                         747
```